United States Patent
Naughton et al.

(10) Patent No.: US 6,395,538 B1
(45) Date of Patent: May 28, 2002

(54) METHOD AND SYSTEM FOR PROVIDING REAL-TIME, IN SITU BIOMANUFACTURING PROCESS MONITORING AND CONTROL IN RESPONSE TO IR SPECTROSCOPY

(75) Inventors: Raymond A. Naughton, West River; Thomas R. Rohrer, Hagerstown; Reiner L. Gentz, Rockville, all of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/616,894

(22) Filed: Jul. 14, 2000

Related U.S. Application Data

(60) Provisional application No. 60/157,863, filed on Oct. 6, 1999, provisional application No. 60/144,071, filed on Jul. 16, 1999, and provisional application No. 60/151,918, filed on Sep. 1, 1999.

(51) Int. Cl.[7] ............................ C12M 1/34; C12N 13/00
(52) U.S. Cl. .................. 435/288.7; 435/173.1; 435/173.7
(58) Field of Search .................. 435/173.1, 173.7, 435/988.7

(56) References Cited

U.S. PATENT DOCUMENTS

| | | | |
|---|---|---|---|
| 991,025 A | * 5/1911 | Wright et al. | |
| 4,064,015 A | 12/1977 | Nyiri et al. | 195/108 |
| 4,986,916 A | 1/1991 | Hickey | 210/603 |
| 5,233,876 A | 8/1993 | LaPack et al. | 73/863.23 |
| 5,262,961 A | 11/1993 | Farone | 364/500 |
| 5,506,117 A | 4/1996 | Andrews et al. | 435/29 |
| 5,679,954 A | 10/1997 | Soloman | 250/339.08 |
| 5,710,251 A | 1/1998 | Vellekamp et al. | 530/351 |
| 5,712,797 A | 1/1998 | Descales et al. | 364/499 |
| 5,750,361 A | 5/1998 | Prusiner et al. | 435/23 |
| 5,756,672 A | 5/1998 | Builder et al. | 530/350 |
| 5,808,006 A | 9/1998 | Builder et al. | 530/399 |
| 5,830,713 A | 11/1998 | Ferrari et al. | 435/91.1 |
| 5,861,382 A | 1/1999 | Cohen et al. | 514/53 |
| 5,866,430 A | 2/1999 | Grow | 436/172 |
| 5,912,327 A | 6/1999 | Li et al. | 530/412 |
| 6,070,128 A | 5/2000 | Descales et al. | 702/30 |
| 6,100,526 A | * 8/2000 | Mayes | |
| 2001/0020091 A1 | * 9/2001 | Buchanan et al. | |

FOREIGN PATENT DOCUMENTS

| | | |
|---|---|---|
| DE | 195 31 595 | 3/1997 |
| JP | 11-89564 | 4/1999 |
| WO | WO 99/34220 | 7/1999 |

OTHER PUBLICATIONS

Bachinger, Th. et al., "Estimation of biomass and specific growth rate in a recombinant *Escherichia coli* batch cultivation process using a chemical multisensor array," *J. Biotechnol.* 60:55–66 (Feb. 1998).

(List continued on next page.)

*Primary Examiner*—Jon P. Weber
(74) *Attorney, Agent, or Firm*—Sterne, Kessler, Goldstein & Fox P.L.L.C.

(57) ABSTRACT

A method and system for providing real-time, biomanufacturing process monitoring and control in response to infrared (IR) spectroscopic fingerprinting of a biomolecule. IR spectroscopy is used to fingerprint an active biomolecule in situ in a biomanufacturing process. In one embodiment, Fourier Transform Infra-red spectroscopy (FTIR) is used to determine whether an active or aged biomolecule is present in stages of a biomanufacturing process. In one preferred example, the biomanufacturing process manufactures a biomaterial in bulk. The biomanufacturing process has four stages: bioproduction, recovery, purification, and bulk storage. FTIR spectroscopy is used to monitor the optimization of each process step by providing feedback controls, and to fingerprint in real-time, in situ whether active biomolecules are present in each stage.

27 Claims, 13 Drawing Sheets

OTHER PUBLICATIONS

Bartl, F. et al., "Proton relay system in the active site of maltodextrinphosphorylase via hydrogen bonds with large proton polarizability: an FT–1R difference spectroscopy study," *Eur. Biophys. J.* 28:200–207 (Mar. 1999).

Bauer, H.H. et al., "Interfacial Adsorption and Aggregation Associated Changes in Secondary Structure of Human Calcitonin Monitored by ATR–FTIR Spectroscopy," *Biochem.* 33:12276–12282 (1994).

Boaz, J.R. et al., "Off–Line, Real–Time, FT–IR Analysis of a Process Step in Imipenem Production," *SPIE—The Intl. Soc. for Optical Engineer., Optically Based Methods for Process Analysis* 1681:319–333 (1992).

Chen, B. et al., "Influence of Calcium Ions on the Structure and Stability of Recombinant Human Deoxyribonuclease I in the Aqueous and Lyophilized States," *J. Pharmaceut. Sci.* 88:477–482 (Apr. 1999).

Cheung, H.–Y. et al., "Real–time monitoring of *Bacillus subtilis* endospore components by attenuated total reflection Fourier–transform infrared spectroscopy during germination," *Microbiol.* 145:1043–1048 (May 1999).

Doak, D.L. and J.A. Phillips, "In Situ Monitoring of an *Escherichia coli* Fermentation Using a Diamond Composition ATR Probe and Mid–infrared Spectroscopy," *Biotechnol. Prog.* 15:529–539 (May–Jun. 1999).

Dubois, J. et al., "Fourier Transform Infrared Spectroscopic Investigation of Temperature– and Pressue–Induced Disaggregation of Amyloid A," *Scand. J. Immunol.* 49:376–380 (Apr. 1999).

Faulkner, J., "The Evolving Role of Product Characterization During Developement," *Biopharm* 13:26–34 (Jun. 2000).

Fu, K. et al., "FTIR characterization of the secondary structure of proteins encapsulated within PLGA microspheres," *J. Controlled Release* 58:357–366 (Apr. 1999).

Gill, A. et al., "Bioprocess monitoring: An optical biosensor for rapid bioproduct analysis," *J. Biotechnol.* 65:69–80 (Oct. 1998).

Landau, R.N. et al., "In–situ Fourier transform infrared and calorimetric studies of the preparation of a pharmaceutical intermediate," *Process Control & Quality* 7:133–142 (1995).

Li, T. et al., "Interactions between NFκB and Its Inhibitor iκB: Biophysical Characterization of a NFκB/iκB–α Complex," *J. Protein Chem.* 17:757–763 (Nov. 1998).

Li–Shi, Y. et al., "Fourier Transform Infrared (FTIR) Spectroscopy for Monitoring Airborne Gases and Vapors of Industrial Hygiene Concern," *Am. Ind. Hyg. Assoc. J.* 50:354–359 (1989).

Marose, S. et al., "Optical sensor systems for bioprocess monitoring," *TIBTECH* 17:30–34 (Jan. 1999).

McGovern, A.C. et al., "Rapid analysis of the expression of heterologous proteins in *Escherichia coli* using pyrolysis mass spectrometry and Fourier transform infrared spectroscopy with chemometrics: application to α2–interferon production," *J. Biotechnol.* 72:157–167 (Jul. 1999).

Naumann, D. et al., "Microbiological characterizations by FT–IR spectroscopy," *Nature* 351:81–82 (1991).

Neault, J.F. and H.A. Tajmir–Riahi, "Structural Analysis of DNA–Chlorophyll Complexes by Fourier Transform Infrared Difference Spectroscopy," *Biophys. J.* 76:2177–2182 (Apr. 1999).

Noguchi, T. et al., "Comparative FTIR Analysis of the Microenvironment of $Q_A$ in Cyanide–Treated, High pH–Treated and Iron–Depleted Photosystem II Membrane Fragments," *Biochem.* 38:4846–4852 (Apr. 1999).

Orth, H.C.J. et al., "Isolation, Purity Analysis and Stability of Hyperforin as a Standard Material from *Hypericum perforatum* L.," *J. Pharm. Pharmacol.* 51:193–200 (Feb. 1999).

Rein, A.J., "Pharmaceutical process development and optimization using in–site Fourier transform infrared spectroscopy," *SPIE—The Intl. Soc. for Optical Engineer., Optically Based Methods for Process Analysis* 1681:374–380 (1992).

Remmele, Jr., R.L. et al., "Real–Time in Situ Monitoring of Lysozyme During Lyophilization Using Infrared Spectroscopy: Dehydration Stress in the Presence of Sucrose," *Pharmaceut. Res.* 14:1548–1555 (1997).

Shank, S. et al., "On–line IR analyzer system to monitor cephamycin C loading on ion exchange resin," *SPIE—The Intl. Soc. for Optical Engineer., Optically Based Methods for Process Analysis* 1681:349–355 (1992).

Uversky, V.N. et al., "Association of partially–folded intermediates of staphylococcal nuclease induces structure and stability," *Protein Sci.* 8:161–173 (Jan. 1999).

van Thor, J.J. et al., "Characterization of the Photoconversion of Green Fluroescent Protein with FTIR Spectroscopy," *Biochem.* 37:16915–16921 (Dec. 1998).

White, R.L. and D.E. Roberts, "Fourier Transform Infrared Detection of Pyruvic Acid Assimilation by *E. coli*," *Anal. Chem.* 57:2487–2491 (1985).

Yang, X.–M. et al., "Production of recombinant human interferon–$\alpha_1$ by *Escherichia coli* using a computer–controlled cultivation process," *J. Biotechnol.* 23:291–301 (1992).

Barth, A. et al., "Time–resolved Infrared Spectroscopy of the $Ca^{2+}$–ATPase," *J. Biol. Chem.* 271:30637–30646, The American Society for Biochemistry and Molecular Biology, Inc., Bethesda, MD (1996).

Barton II, F.E. et al., "Quality Assessment of Agricultural and Food Products by Spectroscopic Methods," TEKTRAN, United States Department of Agriculture, Agricultural Research Service, Beltsville, MD (1995).

Chen, B. et al., "Influence of Calcium Ions on the Structure and Stability of Recombinant Human Deoxyribonuclease I in the Aqueous and Lyophilized States," *J. Pharm Sci* 88:477–482, American Chemical Society, Washington, DC and American Pharmaceutical Association, Washington, DC (Apr. 1999).

Delwiche, S.R. et al., "Protein Content Measurement in Hard Red Winter Wheat by Near–Infrared Spectroscopy on Whole Grain: Collaborative Study," TEKTRAN, United States Department of Agriculture, Agricultural Research Service, Beltsville, MD (1996).

Ejima, D. et al., "High Yield Refolding and Purification Process for Recombinant Human Interleukin–6 Expressed in *Escherichia coli*," *Biotechnol. and Bioeng.* 62:301–310, John Wiley & Sons, Inc., New York, NY (Feb. 1999).

Farrell Jr., H.M., et al., "Environmental Effects on Disulfide Bonding Patterns of Bovine K–Casein," TEKTRAN, United States Department of Agriculture, Agricultural Research Service, Beltsville, MD (1997).

Farrell Jr., H.M. et al., "Environmental Influences on Purified K–Casein: Disulfide Interactions," TEKTRAN, United States Department of Agriculture, Agricultural Research Service, Beltsville, MD (1997).

Fukuyama, Y. et al., "A Study on the Differences Between Oral Squamous Cell Carcinomas and Normal Oral Mucosas Measured by Fourier Transform Infrared Spectroscopy," *Biospectroscopy* 5:117–126, John Wiley & Sons, Inc., New York, NY (Apr. 1999).

Huang, X. et al., "Synthesis and characterization of a series of novel glutamic γ–$^{15}$N–anilide dipeptides," *J. Pept. Res.* 53:126–133, Munksgaard International Publishers Ltd., Copenhagen, Denmark (Feb. 1999).

Huang, Z. et al., "Scrapie prions: a three–dimensional model of an infectious fragment," *Folding & Design* 1:13–19, Current Biology Ltd., London, England (1995).

Miháály, L. and Martin, M.C., *Problem: Fourier Transform Infrared Spectroscopy* (visited Apr. 1999) <http://solidstate.physics.sunysb.edu/book/prob/node111.html>.

PhotoMetrics, Inc., *Fourier Transform Infrared Spectroscopy (FTIR)*, (visited Apr. 1999) <http://www.photometrics.net/ftir.html>.

Smith, B.C., *Fundamentals of Fourier Transform Infrared Spectroscopy*, CRC Press, Washington, DC (1996).

Schreiber, F. et al., "Stability Determination of a Penicillin Precursor with a ReactIR 1000 and the Resultant Improvement on the Production Process," in *ASI Applied Systems Reaction Insights*, vol. II, ASI Applied Systems, Inc., Millersville, MD, pp. 1–7 (1996).

Surface Science Laboratories, *Fourier Transform Infrared Spectroscopy* (visited Jan. 2001) <http://www.surface-science.com/ftir.html>.

West Coast Analytical Service (WCAS), Inc., *FTIR—Fourier Transform Infrared Spectroscopy* (visited Apr. 1999) <http://www.wcaslab.com/tech/tbftir.htm>.

Yang, X.–M., "Optimization of a cultivation process for recombinant protein production by *Escherichia coli*," *J. Biotechnol.* 23:271–289, Elsevier Science BV, Amsterdam, Netherlands (1992).

Ying, L.–S. et al., "Fourier Transform Infrared (FTIR) Spectroscopy for Monitoring Airborne Gases and Vapors of Industrial Hygiene Concern," *Am. Ind. Hyg. Assoc. J.* 50:354–359, American Industrial Hygiene Association, Akron, OH (1989).

Zhang, N. and Jones, B.L., "Purification and Partial Characterization of a 31 KD Cysteine Endoproteinase From Germinated Barley," TEKTRAN, United States Department of Agriculture, Agricultural Research Service, Beltsville, MD (1995).

"User's Guide: ReactIR™ 1000 and ReactIR MP™ Mobile Reaction Analysis Systems, Third Edition," ASI Applied Systems, LLC, Millersville, MD (1997).

"ReactIR Reaction Analysis Systems," ASI Applied Systems, Inc., pp. 1–11 (1993).

"Product Data Sheet: Comp™ Probes: For ReactIR™ Reaction Analysis and Process Monitoring Systems: *In Situ, Real–Time Reaction Monitoring*," ASI Applied Systems, Inc., Millersville, MD (1996).

"Application Notes: Identification and Monitoring of Intermediates in Reactions Carried Out at Low Temperature— The Synthesis of β–Lactam Antibiotics," ASI

* cited by examiner

METHOD AND SYSTEM FOR PROVIDING REAL-TIME, IN SITU BIOMANUFACTURING PROCESS MONITORING AND CONTROL IN RESPONSE TO IR SPECTROSCOPY

CROSS-REFERENCE TO RELATED APPLICATIONS

The present application claims benefit to the filing dates of U.S. Provisional Application No. 60/157,863, filed Oct. 6, 1999, U.S. Provisional Application No. 60/151,918, filed Sep. 1, 1999, and U.S. Provisional Application No. 60/144,071, filed Jul. 16, 1999, each of which is incorporated by reference herein in its entirety.

BACKGROUND OF THE INVENTION

1. Field of the Invention

The present invention pertains to the fields of biomanufacturing and infra-red spectroscopy.

2. Related Art

Biomaterial is used as component material in biomanufacturing. For example, biomaterial is a component material in biologically active pharmaceutical ingredient (BAPI) manufacture. Such biomaterial can include, but is not limited to, proteins, DNA fragments, cDNA, and messenger RNA. Biomaterial is generally made up of one or more biomolecules.

Quality monitoring and control are especially important in biomanufacturing. One conventional approach to quality control is to view the biomanufacturing process as a "black box." Clinical tests and trials are performed on subjects using the final biomanufactured product (i.e., a pharmaceutical). Such clinical testing can be costly and subject to rigorous Federal Drug Administration regulation.

Off-line sampling and analytical techniques are also used to monitor and control processes in biomanufacturing. Infrared spectroscopy, including FTIR, is used to study samples drawn from a biomanufacturing process off-line. Drawing such samples, however, can be invasive to a biomanufacturing process creating sterilization and other problems. Off-line sampling also has limited value in the quality control of commercial biomanufacturing. Such off-line analysis can involve time-consuming analyte or sample preparation and may only approximate in situ conditions in a stage of biomanufacture. Off-line sampling is too slow for practical commercial biomanufacturing, such as, BAPI manufacture. Data results even from an IR spectrometer are obtained after too long a delay to provide an adequate quality control response to a biomanufacturing stage.

Currently available processes for measuring the stability of biomolecules in bulk storage are tedious, expensive, and time consuming. According to current practice, accelerated stability studies are used to determine the "shelf life" of a biomolecule formulation. These studies involve storage at elevated temperatures, and analysis of the stability of the biomolecule over time, done by sampling techniques. These results are then mathematically fitted to lower temperatures. Although these accelerated studies are allowed by the Food and Drug Administration for pharmaceuticals, the limits are very narrow, because the error can be significant. Since the error in these studies can be high, manufacture of biomolecule formulations requires the skilled artisan to include a certain amount of overage in any given formulation, to account for any unknown amount of degradation. This can be very costly.

Infrared spectroscopy (IR) has long been used in the evaluation of chemical compounds. Fourier Transform Infrared Spectroscopy (FTIR) has been used to identify and evaluate organic and inorganic materials or compounds. See, e.g., Smith, B., *Fundamentals of Fourier Transform Infrared Spectroscopy*, CRC Press (1996), which is incorporated herein by reference. Using FTIR, spectral data is collected and converted from an interference pattern to a spectrum. The system provides for subtractive elimination of background spectra, such that particular chemical compounds can be identified by a molecular "fingerprint." Organic compounds have been studied using IR spectroscopy, including FTIR spectroscopy, in off-line sampling or analytic applications, but not as a real time method of monitoring and controlling the course of a bioprocess in commercial biomanufacturing.

SUMMARY OF THE INVENTION

As recognized by the inventors, what is needed is a method and system for providing real-time, in situ monitoring and control for a complete biomanufacturing process. A biomolecule and its production needs to be monitored and appropriately characterized for the product's stage of development, in situ and in real-time in different stages of a commercial biomanufacturing process. See, e.g., Faulkner, J., *BioPharm*, June 2000:26–34, the disclosure of which is incorporated herein by reference in its entirety. Control strategies in response to real-time IR spectroscopic data are needed in each stage of a biomanufacturing process.

The present invention provides real-time, biomanufacturing process monitoring and control in response to infra-red (IR) spectroscopic monitoring of the biomanufacturing process, and fingerprinting of a biomolecule. IR spectroscopy data is used to provide optimal production control for a biomolecule process and is then used to fingerprint the biomolecule in situ in a biomanufacturing process. In one embodiment, Fourier transform infrared spectroscopy (FTIR) is used to monitor the production of a biomolecule and to fingerprint, both qualitatively and quantitatively, the biomolecule at different stages of a biomanufacturing process. In one example, such FTIR fingerprinting is used to differentiate, in real time, between an active or a non-active biomolecule during the stages of a biomanufacturing process, and to control the biomanufacturing process through feedback inputs to optimize the yield of the active form of the biomolecule.

In one preferred embodiment, the biomanufacturing process manufactures a biomaterial in bulk. The biomanufacturing process has four stages: bioproduction (e.g., fermentation), recovery, purification, and bulk formulation and storage. In the bioproduction stage, IR spectroscopy is used (a) to monitor and control homeostasis of the bioproduction reaction, thereby maintaining optimal conditions for increase in biomass and biomolecule synthesis, (b) in some embodiments requiring a two-step growth and induction process, to determine or alternatively detect the optimal time to induce biomolecule synthesis, (c) in some embodiments where the biomolecule is in solution during bioproduction, to monitor, in real-time, in situ, the proportion of the pharmacologically active form of a biomolecule relative to inactive forms, (d) to periodically or continuously adjust the conditions of the biomanufacturing process in order to preferentially favor or alternatively optimize the yield of the pharmacologically active form of the biomolecule, and/or (e) any full or partial combination of (a) through (d). In the recovery and purification stages, IR spectroscopy is used to monitor, in real-time, in situ, the proportion of the pharmacologically active form of a biomolecule relative to inactive forms, and to periodically or continuously adjust the conditions of the biomanufacturing process in order to optimize the yield of the pharmacologically active form of the biomolecule. The presence of an appropriately-characterized biomolecule is verified in situ and in real-time in different stages of a commercial biomanufacturing process. In the bulk storage stage, IR spectroscopy is used to continuously monitor the quality of the stored biomolecule to precisely determine the pharmacological activity of the formulation when it is processed for final finish and fill, and to provide immediate feedback adjustments in the storage conditions to optimize and extend storage. A real-time stability curve during bulk storage will also allow for accurate prediction or extrapolation of the stability of the formulation after finish and fill, thereby minimizing the need for overage. Real-time IR monitoring of bulk storage also provides the potential to automate and accelerate product stability determinations.

Control strategies in response to real-time IR spectroscopic data are provided in each stage of BAPI manufacturing. IR analysis is provided in situ, in real-time to control a bioproduction stage, one or more steps of a recovery stage, one or more steps of a purification stage and/or a bulk storage stage. In this way, both production and development time and costs are minimized.

In addition, biomanufacturing process monitoring and control in response to infra-red (IR) spectroscopic monitoring of the biomanufacturing process, and fingerprinting of a biomolecule can be used to ensure consistency in biomanufacturing processes carried out in different biomanufacturing plants. This advantage of the present invention provides flexibility to the manufacturer to outsource production, and thereby more efficiently control production without sacrificing quality control.

Further embodiments, features, and advantages of the present inventions, as well as the structure and operation of the various embodiments of the present invention, are described in detail below with reference to the accompanying drawings.

BRIEF DESCRIPTION OF THE FIGURES

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE PREFERRED EMBODIMENTS

Figure 1:
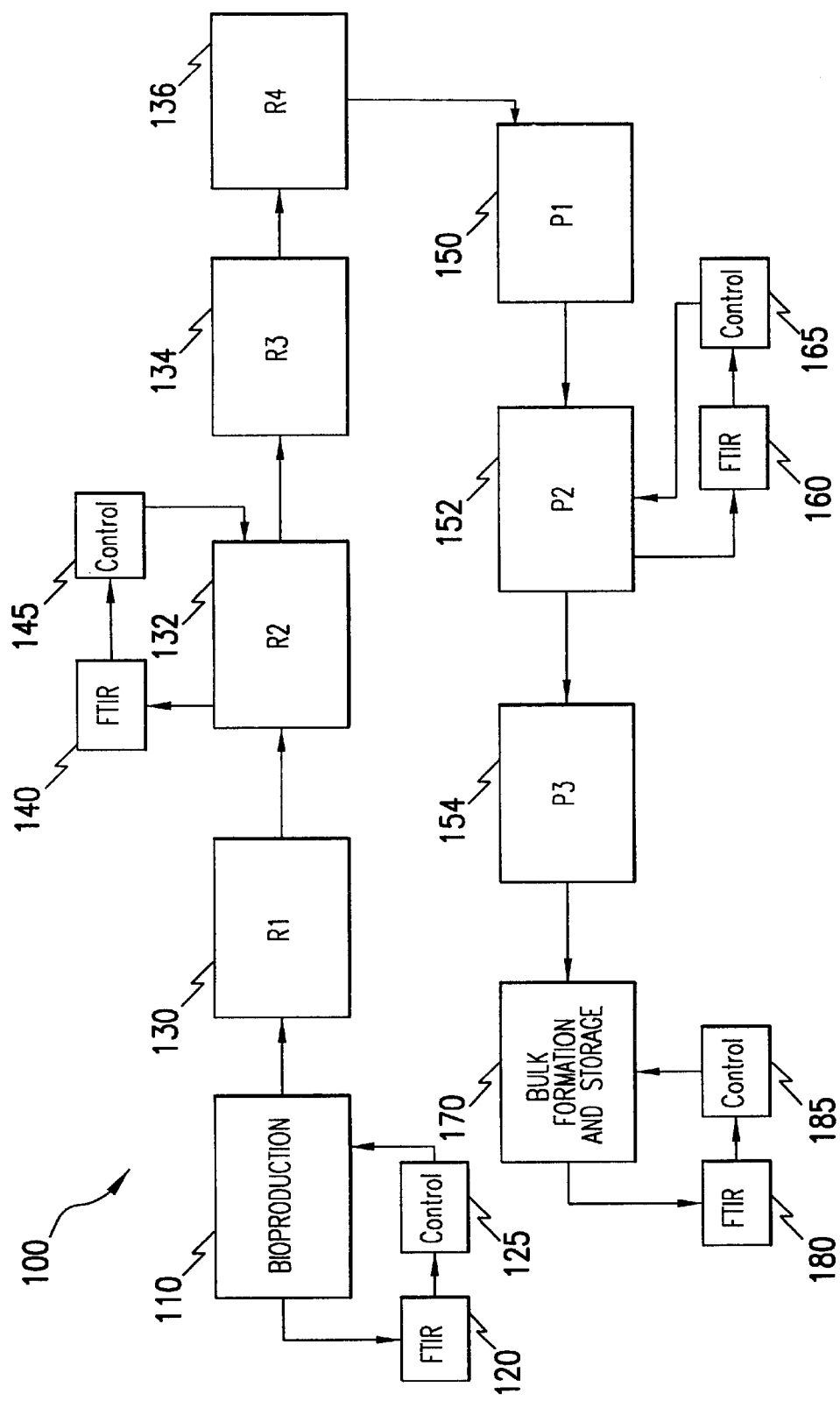
FIG. 1 shows an example biomanufacturing system with real-time FTIR process monitoring and control at certain process steps according to one embodiment of the present invention. R1, R2, R3, and R4 refer to steps in the recovery stage. P1, P2, and P3 refer to steps in the purification stage.

Table of Contents
I. Terminology
II. Real Time Process Control in a Biomanufacturing Process
   A. Monitoring and Control of a Biomanufacturing Process
   B. IR Spectroscopic Fingerprinting of a Biomolecule
III. Real Time Process Control in Bioproduction
IV. Real Time Process Control in Recovery
V. Real Time Process Control in Purification
VI. Real Time Process Control in Bulk Formulation and Storage
   A. Real-Time Monitoring and Control Including FTIR
   B. Automated Accelerated Storage Studies Based on FTIR Monitoring
VII. Example Computer System

VIII. EXAMPLES

Example 1

Biomanufacturing Process for Human Interleukin-10 Produced in *Escherichia coli* Using FTIR Monitoring and Control A. Fermentation
   B. Recovery
   C. Purification
   D. Bulk Storage
IX. Conclusion
I. Terminology The term "biomolecule" refers to any chemical species which derives its effect on living cells, systems, or organisms by virtue of orthodox secondary, tertiary, and/or quaternary molecular structures, in addition to primary chemical structure. As used herein, the term "biomolecule" refers to one or more biomolecules, and includes but is not limited to, the following: proteins, polypeptides, or complexes, analogs, or derivatives thereof; DNA, RNA, polynucleotides, or complexes, analogs, or derivatives thereof; plasmid vectors; final products, i.e., commercial embodiments or processed forms of the product; intermediate products, i.e., unprocessed products, e.g., prior to conversion to an active species, or denatured species; peptide nucleic acids (PNA), monoclonal or polyclonal antibodies, derivatives of the commercial embodiment, i.e., antibodies specific to the commercial embodiment or chemically modified forms of the commercial embodiment; or fragments, complexes, or analogs of the commercial embodiment.

Biomolecules of the present invention include antibodies and T-cell antigen receptors (TCR) which specifically bind the polypeptide biomolecules of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin including birds and mammals. Preferably, the antibodies are human, murine, rabbit, goat, guinea pig, camel, horse, or chicken. Biomolecules of present invention further includes monoclonal, polyclonal, chimeric, humanized, and human monoclonal and human polyclonal antibodies which specifically bind polypeptide biomolecules of the present invention. The present invention further includes antibodies which are anti-idiotypic to antibody biomolecules of the present invention.

Preferred biomolecules of the present invention include, but are not limited to, the biomolecules listed in Table 1. Each of these biomolecules is described in a U.S. or a foreign patent publication, which are also listed in Table 1. The references listed in Table 1 are each incorporated herein by reference.

TABLE 1

| Biomolecule | Reference |
| --- | --- |
| Interleukin-1 beta converting enzyme-like apoptotic protease-7 | EP-807686-A2 |
| Human ICE LAP-6 polypeptide | EP-808904-A2 |
| Human cytokine/peptide receptor, HR-1 receptor | EP-812913-A2 |
| Human cathepsin K gene | EP-812916-A2 |
| Homo sapiens arginase II gene | EP-825260-A2 |
| Human integrin ligand polypeptide ITGL-TSP HPMBQ91 | EP-874050-A2 EP-892053-A2 |
| cDNA encoding human MYH | J10057076-A |
| Death domain containing receptor polypeptide (DR3-V1) | J11000170-A |
| cDNA encoding human homologue of *E. coli* AlkB gene, hABH | US5618717-A |
| cDNA encoding human oxalyl-CoA decarboxylase | US5635616-A |
| cDNA encoding human ubiquitin conjugating enzyme 7 | US5650313-A |
| Human GABA-A receptor epsilon subunit | US5654172-A |
| Human MutT2 (hMutT2) protein | US5695980-A |
| cDNA sequence of the putative mature potassium channel 1 protein | US5710019-A |
| Human elastase IV | US5710035 |
| Nucleotide sequence of human inositol monophosphatase-H1 | US5716806-A |
| Human lymphoid-specific transcription factor NERF-1 | US5721113-A |
| Human DNA topoisomerase I alpha | US5723311-A |
| Human FGF-13 | US5728546-A |
| Polynucleotide sequence of a colon-specific gene | US5733748-A |
| Human vascular IBP-like growth factor | US5747280 |
| Human AlkB polypeptide | US5747312 |
| Nucleotide sequence of the G-protein coupled receptor | US5750370-A |
| G-protein coupled prostate tissue receptor designated HPRAJ70 | US5756309-A |
| Neurotransmitter transporter | US5759854 |
| Human fibroblast growth factor 11 | US5763214-A |
| Human G-protein coupled receptor | US5763218-A |
| Nucleotide sequence of fibroblast growth factor-15 (FGF-15) | US5773252-A |

TABLE 1-continued

| Biomolecule | Reference |
| --- | --- |
| Nucleotide sequence of the human G-protein chemokine receptor HGBER32 | US5776729-A |
| Human small CCN-like growth factor | US5780263-A |
| Arginase II | US5780286 |
| Human geranyl geranyl pyrophosphate synthase | US5786193-A |
| Human prostatic specific reductase | US5786204 |
| Paraoxonase polypeptides and use therefor | US5792639 |
| Amine transporter | US5798223-A |
| Human G-protein adrenergic receptor | US5817477-A |
| Nucleic acids and cells for recombinant production of fibroblast growth factor-10 | US5817485 |
| Human DNase | US5830744-A |
| Corpuscles of stannius protein stanniocalcin | US5837498 |
| Human cytostatin I polypeptide | US5844081-A |
| Ubiquitin conjugating enzyme (UCE) 7 | US5849286-A |
| Human elastate IV | US5851814 |
| Human DNA ligase III | US5858705-A |
| Human amine transporter | US5859200 |
| Human C5a receptor protein | US5861272-A |
| Cathepsin K gene | US5861298 |
| cDNA sequence of a human colon specific gene | US5861494-A |
| Polynucleotide encoding a human chemotactic protein | US5866373 |
| DNA encoding retinotic acid receptor epsilon | US5869284 |
| Human G-protein coupled receptor, HCEGH45 | US5869632-A |
| Superoxide dismutase-4 | US5871729 |
| Human NAF-1 DNA | US5871969-A |
| Human h4-IBBSV receptor DNA | US5874240-A |
| Antibodies to corpuscles of stannius protein stanniocalcin | US5877290 |
| Human chemotactic protein | US5880263 |
| Polynucleotides encoding chemokine alpha-2 | US5910431 |
| Arginase II polypeptide | US5912159-A |
| Method of purifying chemokines from inclusion bodies | US5912327 |
| Human deoxycytidine kinase 2 | US5914258 |
| Polynucleotides encoding extra cellular/epidermal growth factor HCABA58X polypepides | US5916769 |
| Human cystatin F | US5919658 |
| Polynucleotides encoding haemopoietic maturation factor | US5922572 |
| Human amine receptor | US5928890 |
| Human geranylgeranyl pyrophosphate synthetase | US5928924 |
| Human ABH | US5929225 |
| Vascular endothelial growth factor 2 | US5932540 |
| Polynucleotides encoding vascular endothelial growth factor 2 | US5935820 |
| Polynucleotides encoding human G-protein coupled receptor HIBEF51 | US5942414 |
| CD44-like protein and nucleic acids | US5942417 |
| Human oxalyl-coa decarboxylase | US5945273 |
| Human hematopoietic-specific protein | US5945303 |
| Cytostatin III nucleic acids encoding | US5945309 |
| Ubiquitin conjugating enzymes 7 8 and 9 | US5945321 |
| Human G-protein receptor HPRAJ70 | US5948890 |
| DNA encoding the chemotactic cytokine III | US5952197 |
| Macrophage inflammatory protein-3 | WO9517092-A |
| Haematopoietic maturation factor | WO9519985-A1 |
| hGHV-2(88) growth hormone splice variant | WO9520398-A |
| Human osteoclast-derived cathepsin-O | WO9524182-A1 |
| cDNA encoding stanniocalcin from Corpuscles of Stannius | WO9524411-A1 |
| Human fibroblast growth factor 10 | WO9524414-A1 |
| Human transforming growth factor alpha-H1 polynucleotide | WO9524466-A1 |
| DNA encoding vascular endothelial growth factor 2 | WO9524473-A1 |
| DNA encoding mature Bone Morphogenic Protein-10 | WO9524474-A1 |
| Human superoxide-dismutase-4 polynucleotide | WO9527781-A1 |
| Human DNase precursor | WO9530428-A1 |
| Human monocyte chemotactic protein-4 | WO9531467-A1 |
| Human macrophage migration inhibitory factor-3 (MIF-3) | WO9531468-A1 |
| Human DNA-topoisomerase-I alpha protein | WO9531538-A1 |
| Human neurotransmitter transporter protein | WO9531539-A1 |
| Human interleukin-6 splice variant DNA | WO9532282-A1 |
| Human FLAP II | WO9535372-A1 |
| Retinoic acid receptor epsilon | WO9600242-A1 |
| ICE-like apoptosis protease-1 | WO9600297-A1 |
| Human elastase IV gene | WO9601270-A1 |

TABLE 1-continued

| Biomolecule | Reference |
|---|---|
| Human serum paraoxonase | WO9601322-A1 |
| Connective tissue growth factor-2 | WO9601896-A |
| Human K + channel 1 | WO9603415-A1 |
| Calcitonin gene-related peptide receptor | WO9604928-A1 |
| cDNA encoding a human calcitonin receptor | WO9605221-A |
| Human adrenergic G-protein coupled receptor | WO9605225-A1 |
| G-protein coupled receptor | WO9605226-A1 |
| Human chemokine beta-4 | WO9605856-A1 |
| Chemokine beta-9 | WO9606169-A1 |
| Human GABA-A receptor epsilon subunit | WO9606862-A |
| Inositol-monophosphatase-H1 full-length gene | WO9608557-A1 |
| Transcription factor IIA small subunit | WO9609311-A1 |
| TAR-3 | WO9611259-A1 |
| Human endothelin-bombesin receptor | WO9611946-A1 |
| Hypoxanthine guanine phosphoribosyl transferase 2 | WO9612501-A1 |
| Human homologue of bacterial AlkB gene (hABH) | WO9612791-A1 |
| Human interleukin-I-converting enzyme-like apoptosis protease-3 | WO9613603-A1 |
| Tumour necrosis factor-gamma | WO9614328-A1 |
| DNA-ligase-III gene | WO9614394-A1 |
| Stanniocalcin alpha | WO9615147-A1 |
| hMutT2 | WO9615222-A1 |
| Human choline acetyltransferase | WO9615806-A1 |
| Human G-protein coupled receptor | WO9616087-A1 |
| Vascular IBP-like growth factor | WO9617931-A1 |
| Tissue inhibitor of metalloproteinase-4 | WO9618725-A1 |
| Human prostatic growth factor | WO9618730-A1 |
| Human deoxycytidine kinase 2 | WO9621724-A1 |
| Human geranylgeranyl pyrophoshate synthetase (GGPPS) | WO9621736-A1 |
| Prostate specific reductase | WO9622360-A1 |
| Ubiquitin conjugating enzyme 7 | WO9623410-A1 |
| Human chemokine alpha-1 | WO9624668-A1 |
| Human chemokine beta-11 | WO9624668-A1 |
| Keratinocyte growth factor 2 | WO9625422-A1 |
| Human G-protein coupled receptor | WO9625432-A1 |
| Human amine transporter | WO9627009-A1 |
| Human tumour necrosis factor receptor | WO9628546-A1 |
| Human B-cell translocation gene-2 polypeptide | WO9629401-A1 |
| Human G-protein coupled receptor GPR1 | WO9630406-A1 |
| Human DNA ligase III | WO9630524-A1 |
| Human tumour necrosis factor receptor | WO9634095-A1 |
| Neuropeptide receptor gene | WO9634877-A1 |
| cDNA encoding human cytokine beta-8: a chemo-attractant for leukocytes | WO9634891-A1 |
| Human inhibitor of apoptosis gene 1 | WO9635703-A1 |
| Human uridine diphosphate galactose-4-epimerase | WO9635778-A1 |
| Human transforming growth factor alpha HII | WO9636709-A1 |
| Human G protein gamma-3 subunit | WO9637513-A1 |
| Pineal gland specific gene-1 | WO9639158-A1 |
| Human cystatin E | WO9639418-A1 |
| Human colon specific gene CSG5 | WO9639419-A1 |
| Human criptin growth factor | WO9639420-A1 |
| Human vascular endothelial growth factor 3 | WO9639421-A1 |
| Natural killer cell enhancing factor C | WO9639424-A1 |
| Human bone morphogenic protein-10 | WO9639431-A1 |
| G-protein parathyroid hormone receptor HLTDG74 | WO9639433-A1 |
| Human G-protein receptor HGBER32 | WO9639434-A1 |
| Human G-protein receptor HPRAJ70 | WO9639435-A1 |
| Human G-protein coupled receptor HETGQ23 | WO9639436-A1 |
| Human G-protein chemokine receptor HDGNR10 | WO9639437-A1 |
| Human G-protein thrombin-like receptor | WO9639438-A1 |
| Human G-protein receptor HCEGH45 | WO9639439-A1 |
| Human amine receptor | WO9639440-A1 |
| G-protein coupled receptor | WO9639441-A1 |
| G-protein receptor, HTNAD29 | WO9639442-A1 |
| Human hepatoma-derived growth factor (HDGF-2) | WO9639485-A1 |
| cDNA encoding small CCN-like growth factor | WO9639486-A1 |
| cDNA encoding transforming growth factor alpha-HI | WO9639497-A1 |
| Human fibroblast growth factor 14 cDNA (ATCC #97148) | WO9639506-A1 |
| Human fibroblast growth factor 11 cDNA (ATCC #97150) | WO9639507-A1 |
| Fibroblast growth factor 13 | WO9639508-A1 |
| Human fibroblast growth factor 15 | WO9639509-A1 |
| Human vascular endothelial growth factor 2 | WO9639515-A1 |
| Human cytokine beta-13 cDNA (ATCC 97113) | WO9639521-A1 |
| Human chemokine beta-11 | WO9639522-A1 |
| Human colon specific protein | WO9639541-A1 |
| Human monocyte chemotactic protein-4 polypeptide | WO9640762-A1 |
| Human breast specific gene BSG15, clone HBNAC96 | WO9702280-A1 |
| Human cytostatin II | WO9711970-A1 |
| Human mammary transforming protein | WO9717358-A1 |
| Human stem cell antigen 2 | WO9718224-A1 |
| Human smooth muscle cell-derived migration factor | WO9719704-A1 |
| Growth factor receptor-binding protein 2 homologue Grb2-1 | WO9720573-A1 |
| Human osteo antiviral protein DNA | WO9722623-A1 |
| Human chemotactic cytokine I DNA | WO9723640-A1 |
| Human ATP receptor | WO9724929-A1 |
| Human Immune Cell Cytokine-like Hormone (HLHDC84) DNA | WO9725338-A1 |
| Human G-protein chemokine receptor HSATU68 | WO9725340-Al |
| Transforming growth factor alpha HIII polynucleotide | WO9725349-A1 |
| Human cytostatin I gene | WO9727747-A1 |
| Human neuronal attachment factor-1 DNA | WO9729189-A1 |
| Human chemokine beta4 | WO9731098-A1 |
| Human chemotactic cytokine III (CCIII) | WO9732993-A1 |
| DNA encoding a human h4-1BBSV receptor | WO9733898-A1 |
| cDNA encoding human Apoptosis inducing molecule-I (AIM-I) | WO9733899-A1 |
| Human tumour necrosis factor delta | WO9733902-A1 |
| Human mismatch repair MutY cDNA (hMYH gene) | WO9733903-A1 |
| Death domain containing receptor DR3-V1 | WO9733904-A1 |
| cDNA encoding human Arginase II | WO9733985-A1 |
| DNA encoding human Arginase II | WO9733986-A1 |
| Human chemotactic cytokinc II CCII genomic DNA | WO9734013-A1 |
| Human apoptosis inducing molecule II (AIM II) gene | WO9734911-A1 |
| Human endometrial specific steroid-binding factor I DNA | WO9734997-A1 |
| DNA encoding novel human cytokine | WO9734998-A1 |
| Human chemokine alpha-2 | WO9735010-A1 |
| Human chemokine alpha-3 | WO9735027-A1 |
| Human cytostatin III | WO9735028-A1 |
| Human growth factor HTTER36 | WO9735870-A1 |
| Epidermal differentiation factor | WO9735976-A2 |
| Human cystatin F polypeptide | WO9736915-A1 |
| Human chitotriosidase | WO9736917-A1 |
| Human cystatin F encoding sequence | WO9737021-A1 |
| Human natural killer cell activating factor II (NKAF II) DNA | WO9737022-A1 |
| Human extracellular/epidermal growth factor-like protein | WO9738002-A1 |
| Human haematopoietic-specific protein (HSP) DNA | WO9738003-A1 |
| Human extracellular/epidermal growth factor HCABA58X | WO9738012-A1 |
| Human brain P2X-1 receptor | WO9741222-A1 |
| Human DNA repair enzyme RAD | WO9742209-A1 |
| Human G-protein coupled receptor | WO9744359-A1 |
| Human G-protein coupled receptor | WO9744360-A1 |
| Human cathepsin K gene | WO9747642-A1 |
| Human HR-1 receptor | WO9747741-A1 |
| *Homo sapiens* cDNA encoding the HR-1 receptor | WO9747742-A1 |
| Human chemokine beta-15 gene | WO9748807-A1 |
| cDNA encoding a novel G-protein coupled receptor HNFDS78 | WO9803539-A1 |
| Human CD33-like protein | WO9806733-A1 |
| DNA encoding a CD44-like protein | WO9806839-A1 |
| Mutated KGF-2 coding sequence KGF2delta33, 191K/Q | WO9806844-A1 |
| DNA encoding a human chitinase alpha protein | WO9806859-A1 |
| DNA encoding a human chitinase alpha protein variant | WO9806859-A1 |
| *Homo sapiens* pancreas-derived plasminogen activator inhibitor gene | WO9807735-A1 |
| Human XAG growth factor huXAG-1 | WO9807749-A1 |
| Human T1 receptor-like ligand II | WO9807754-A1 |
| Human chemokine beta-16 | WO9807862-A2 |
| Human endokine-alpha | WO9807880-A1 |
| Human TI receptor-like ligand I | WO9807881-A1 |
| Nucleotide sequence of interleukin-19 | WO9808870-A1 |
| Human interleukin-1 receptor accessory molecule | WO9808969-A1 |
| Human chemokine alpha-4 encoding DNA | WO9811138-A1 |
| Human B-cell translocation gene-2 | WO9812204-A1 |
| Modified TR1 receptor | WO9812344-A1 |

TABLE 1-continued

| Biomolecule | Reference |
|---|---|
| Human chemokine beta-11 (Ck beta-11) polypeptide | WO9814477-A1 |
| Human MPIF-1 genomic DNA | WO9814582-A1 |
| Galectin 8 | WO9815624-A1 |
| Brain-associated inhibitor of tissue plasminogen activator | WO9816643-A1 |
| Human TNF receptor related (TR2) gene | WO9818824-A1 |
| Homo sapiens neutrokine alpha protein gene | WO9818921-A1 |
| Human blue-light photoreceptor hCRY2 gene related clone HFCAD18R | WO9820042-A1 |
| Human mucosal adressin cell adhesion molecule-1(a) DNA | WO9820110-A1 |
| Human connective tissue growth factor-3 gene | WO9821236-A1 |
| Human calcitonin receptor cDNA clone HCEPR64 | WO9821242-A1 |
| Fibroblast growth factor-13 | WO9823749-A1 |
| Nucleotide sequence of human G-protein coupled receptor | WO9824900-A1 |
| Human chemokine beta-13 | WO9824908-A1 |
| DNA sequence encoding a human Prt1-like subunit protein | WO9825957-A2 |
| Homo sapiens CESP gene related EST clone | WO9827932-A2 |
| Human parotid secretory protein | WO9828420-A1 |
| Human oncogene induced secreted protein I | WO9828421-A1 |
| Human cell death adaptor molecule RAIDD | WO9828422-A1 |
| Human cortistatin cDNA from clone HEBCI67R | WO9829438-A2 |
| Human TRID genomic DNA | WO9830693-A2 |
| Human tumour necrosis factor receptor-6 alpha | WO9830694-A2 |
| Nucleotide sequence of the HSF cDNA clone 5 | WO9831792-A1 |
| Human extracellular matrix-1 gene | WO9831798-A1 |
| Nucleotide sequence encoding clone HMWGS46 of Prohibitin receptor family | WO9831799-A2 |
| Nucleotide sequence of the cDNA clone CAT-2 (HT3SG28) | WO9831800-A2 |
| I-FLICE-1 and I-FLICE-2 | WO9831801-A1 |
| Primer for FcR-I | WO9831806-A2 |
| Human TACE-like DNA | WO9831818-A2 |
| Human DR4 genomic DNA | WO9832856-A1 |
| Vector pHE4-5 containing human MOGp | WO9833912-A1 |
| Human breast cancer specific gene 1 (BCSG1) | WO9833915-A1 |
| Human tissue factor pathway inhibitor-3 (TFPI-3) | WO9833920-A2 |
| Dendritic cell-derived growth factor (DCDGF) | WO9835039-A1 |
| Human ELL2 cDNA EST AA545429 | WO9837194-A1 |
| Human T1-receptor ligand III clone HSRDN17R DNA sequence | WO9838311-A1 |
| Human secreted protein gene 3 clone HTGEW86 | WO9839446-A2 |
| Human secreted protein gene 100 clone HLQAB52 | WO9839448-A2 |
| Human secreted protein gene 27 clone H2MBT68 | WO9840483-A2 |
| Human death domain containing receptor 5 (DR5) | WO9841629-A2 |
| SV40 promoter containing NF-kB binding sites | WO9842738-A1 |
| Nucleotide sequence encoding Human cytostatin II | WO9844109-A1 |
| Human thymus receptor tyrosine kinase-related clone T09276 | WO9844111-A1 |
| cDNA clone H47991 | WO9844112-A1 |
| DNA encoding human chemokine beta-6 | WO9844118-A1 |
| Human immunoglobulin G (IgG) Fc coding region | WO9845712-A2 |
| Human EEGF genomic DNA | WO9846746-A1 |
| EDG-1-like G-protein coupled receptor | WO9850549-A2 |
| Nucleotide sequence encoding the human antimicrobial protein | WO9851794-A1 |
| cDNA clone W73681.nt which is related to GDNFR-beta sequences | WO9853069-A2 |
| Human tissue plasminogen activator-like protease t-PALP DNA | WO9854199-A1 |
| Human tumour necrosis factor receptor-like protein 8 | WO9854201-A1 |
| Human TNF receptor TR10 DNA | WO9854202-A1 |
| Gene No. 27 encoding human secreted protein | WO9854206-A1 |
| Polynucleotide fragment of gene 56 clone HE2OF09 | WO9854963-A2 |
| Human secreted protein gene 47 clone HOSCZ41 | WO9856804-A1 |
| Novel human tumor necrosis factor receptor TR9 | WO9856892-A1 |
| Human heregulin-like factor | WO9857989-A1 |
| Interferon Stimulating Protein And Uses Thereof | WO9900412 |
| Human cardiotrophin-like cytokine PCR 5'-primer #5 | WO9900415-A1 |
| Human NK-3 prostate specific gene-1 (NKX3.1) | WO9900498-A1 |
| Human secreted protein gene 10 clone HSKGO49 | WO9901020-A2 |
| Human secreted protein gene 122 clone HSVAQ28 | WO9902546-A1 |
| Histidine Kinase Two-component in Candida Albicans | WO9902700 |
| cDNA encoding interleukin-20 | WO9903982-A1 |
| Human secreted protein gene 51 clone HEBCM63 | WO9903990-A1 |

TABLE 1-continued

| Biomolecule | Reference |
|---|---|
| Human secreted protein gene 73 | WO9906423-A1 |
| DNA encoding a human secreted protein | WO9907891-A1 |
| sequence of the human IgGFc region | WO9909152-A1 |
| Human secreted protein cDNA fragment containing gene 33 | WO9909155-A1 |
| Pancreas derived plasminogen activator inhibitor protein | WO9909161-A1 |
| Human nodal protein encoding DNA | WO9909198-A1 |
| Human IgG Fc coding region | WO9910363-A1 |
| Human follistatin-3 coding sequence fragment HLMNX90R | WO9910364-A1 |
| DNA encoding a human secreted protein | WO9911293-A1 |
| Interleukin-17 Receptor-like Protein | WO9914240 |
| EXPRESSION CONTROL SEQUENCES | WO9916858 |
| Human secreted protein cDNA fragment containing gene 93 | WO9918208-A1 |
| Human IgG Fc coding region | WO9919339-A1 |
| Human Tumor Necrosis Factor Receptor-like Proteins TR11, TR11SV1, and TR11SV2 | WO9920758 |
| Human chemokine alpha-6, designated HFCET92 | WO9921575-A1 |
| DNA encoding a human secreted protein | WO9922243-A1 |
| VEGI-alpha cDNA clone HEMFG66 | WO9923105-A1 |
| DNA encoding the human caspase-14 (ERICE) protein | WO9923106-A1 |
| Human IgG Fc coding region | WO9924836-A1 |
| Chemokine Alpha-5 | WO9927078 |
| Human IRAK-2 alpha and beta | WO9927112-A1 |
| Synferon, a Synthetic Type I Interferon | WO9929862 |
| Human Dendriac and Brainiac-3 | WO9931116 |
| 110 Human Secreted Proteins | WO9931117 |
| Keratinocyte Growth Factor-2 Formulations | WO9932135 |
| 36 Human Secreted Proteins | WO9935158 |
| Human Fk506 Binding Proteins | WO9935160 |
| Apoptosis Inducing Molecule II | WO9935262 |
| Human Ependymin | WO9936565 |
| 67 Human Secreted Proteins | WO9938881 |
| Human Cystatin F | WO9938882 |
| 45 Human Secreted Proteins | WO9940100 |
| Human Serine Protease and Serpin Polypeptides | WO9940183 |
| Dendritic Enriched Secreted Lymphocyte Activation Molecule | WO9940184 |
| Therapeutic Uses of Keratinocyte Growth Factor-2 | WO9941282 |
| Apoptosis Inducing Molecule II and Methods of Use | WO9942584 |
| Human Secreted Proteins | WO9943693 |
| Human Secreted Proteins | WO9946289 |
| Angiogenic proteins and Uses Thereof | WO9946364 |
| Oxalyl-CoA decarboxylase | ZA9403789-A |
| Interferon Receptor HKAEF92 | WO 99/62934 |
| Cytokine Receptor Common Gamma Chain-like | WO 99/47538 |
| CTGF-4 | WO 99/62927 |
| Epithelial Specific Transcription Factor PDEF | WO 00/06589 |
| IL-21 and IL-22 | WO 99/61617 |
| Keratinocyte Derived Interferon | WO 00/05371 |
| FGFR-5 | WO 00/24756 |
| Hyaluronan-binding Protein | PCT/US99/30462 |
| 12 Human Secreted Proteins | WO 00/29435 |
| TR12 | WO 00/23572 |
| Prostacyclin-stimulating factor/PGI2 | WO 00/36105 |
| Peptidoglycan Recognition Proteins | WO 00/39327 |
| Chemokine Beta-7 | WO 00/28035 |
| Brainiac-5 | WO 00/39136 |
| Chemokine Beta-10 | PCT/US00/00296 |

The terms "bioactivity," and "bioactive," refer to the state or condition of a biomolecule in which it has a desired chemical or physical property or a desired effect. Examples include, but are not limited to, enzymatic activity, receptor activity, ligand activity, signal transduction activity, pharmacological activity, and therapeutic effect. The terms "pharmacological activity" or "pharmacologically active" refer, inter alia, to the state or condition of a biomolecule in which it creates a desired medicinal or pharmacological effect in the in vivo host. The term also includes additional desired conditions of the biomolecule or a formulation comprising a biomolecule such as stability, toleration by the in vivo host, and bioavailablity.

The term "fingerprint" is used herein to refer to the characteristic IR spectrum of a biomolecule having the desired conformation to produce the desired bioactivity. According to the present invention, biomolecules that share a specific IR "fingerprint" are, by definition, equivalent species of that biomolecule. Methods to determine the fingerprint of a pharmacologically active biomolecule, and to maintain or restore that fingerprint through the entire process train, are disclosed herein.

The term "finish and fill" refers to the process by which a bulk pharmaceutical formulation is processed into packaged units or samples for sale and in some cases, for use in patient populations.

The terms "IR" and "IR spectroscopy" refer to any type of monitoring or measurement of a biomolecule using spectroscopy in the infrared range. These include, but are not limited to mid IR, near IR, far IR, Fourier transform infrared spectroscopy (FTIR), Raman, or other infrared spectroscopic measuring signals. Moreover, the terms "IR" and "IR spectroscopy" can also be used more generally to include NMR, electronic paramagnetic resonance (EPR), mass spectrscopy, circular dichroism (CD), and other spectroscopic methods which rely on detection of signals outside the IR range. IR spectroscopy may be used to measure every possible characteristic chemical bond of a biomolecule and every possible interaction of a biomolecule with itself or with its surrounding environment, including its interaction with another biomolecule. Characteristics of a biomolecule include, but are not limited to, hydrocarbon groups, including alkanes, alkenes, aromatic rings, amide groups, amino groups, alcohol groups, ether groups, ester groups, aldehyde groups, ketone groups, nitrile groups, nitro groups, carboxyl groups, acetyl groups, carbonyl groups, sulfide groups, glycosyl groups, and lipid groups. Interactions include, but are not limited to, hydrogen bonds, disulfide bonds, interactions with metals, e.g., heme groups, formation of homodimers or multimers, formation of heterodimers or multimers, interaction of an enzyme and substrate, interaction of a protein with a nucleic acid, or any interaction which induces a change in the nuclear spin, nuclear magnetic moment, magnetic resonance, fluorescence, resonance, molecule weight, charge, electron density, time of flight, ionization, mass/charge ratio, spin-spin coupling, nuclear Overhauser effect, or excitation state of a biomolecule.

The term "folding of a biomolecule" refers to achieving a characteristic secondary, tertiary, or quaternary structure, or conformation, of that biomolecule. Examples of secondary structures in a protein biomolecule include, but are not limited to alpha helices or beta sheets. Examples of tertiary structures in biomolecules include, but are not limited to monomers, dimers or trimers. Quaternary conformational states in biomolecules are produced by or stabilized with, e.g., hydrogen bonds, Van der Waal's forces, or weak nuclear interactions. A biomolecule of the present invention that has the desired pharmacological activity is "correctly folded," i.e., it has a secondary and tertiary structure required for activity. A biomolecule of the present invention that lacks the desired pharmacological activity may be "improperly folded" may be "proteolytically processed" or may be "denatured." A completely unfolded biomolecule is referred to herein as a "denatured" biomolecule. In certain embodiments, a denatured or improperly folded biomolecule can be refolded to the correct conformation using techniques well known to those skilled in the art, thereby restoring pharmacological activity. In certain embodiments, controlling the level of proteolytic processing can also be minimized and/or maximized using techniques well known to those skilled in the art, thereby restoring or attaining pharmacological activity.

II. Real Time Process Control in a Biomanufacturing Process

A. Monitoring and Control of a Biomanufacturing Process

FIG. 1 shows an example biomanufacturing system 100 with real time process monitoring and control based on FTIR biomolecule fingerprinting according one embodiment of the present invention. Biomanufacturing system 100 is a manufacturing process that produces biologically active pharmaceutical ingredients (BAPI) in bulk. This example biomanufacturing process includes four stages: a bioproduction stage 110, recovery stages 130, 132, 134, and 136, purification stages 150, 152, and 154, and a bulk formulation and storage stage 170. According to this embodiment of the present invention, infrared spectroscopic monitoring and/or biomolecule fingerprinting is performed at the bioproduction stage 110. Infrared spectroscopic biomolecule fingerprinting is performed during at least one recovery step R2 (132), during at least one purification step P2 (152), and during the bulk storage stage 170. It is within the scope of the present invention that infrared spectroscopic biomolecule fingerprinting is performed at additional recovery and purification steps.

The invention further encompasses the use of more than one FTIR analyzer for a particular recovery step, purification step, bioproduction stage, and bulk formulation and storage stage, in real time, as may be required. Moreover, the invention also encompasses the use of more than one control step and/or module for a particular FTIR analyzer. Such additional FTIR analyzers and/or modules/steps could feed data in real time to either the same central processing unit (CPU), a different CPU, or a combination of processors.

In the bioproduction stage 110, an FTIR analyzer report 120 is obtained in real time. Data in the first FTIR analyzer report 120 is provided to a first control step 125. Control step 125 uses the first FTIR analyzer report 120 to control bioproduction stage 110 in real time.

Similarly, a second FTIR analyzer report 140 is obtained in real time in the recovery stage, during at least one recovery step 132. The second FTIR analyzer report 140 is provided to a control step 145. Control step 145 in response controls recovery step 132 in real time. A third FTIR analyzer report 160 is obtained during purification stage, during at least one purification step 152. The third FTIR analyzer report 160 is provided to control step 165. Control step 165 in response controls purification step 152 in real time. A fourth FTIR analyzer report 180 is obtained during the bulk storage stage 170. The fourth FTIR analyzer report 180 is provided to control step 185. Control step 185 in response monitors and controls bulk storage stage 170 in real time.

In this way, real time process control based on infrared spectroscopic biomolecule fingerprinting is provided throughout the biomanufacturing process. Any infrared spectrophotometer can be used to fingerprint the biomolecules in bioproduction stage 110, recovery stage, e.g. at step 132, purification stage, e.g., at step 152, and bulk storage stage 170. In one embodiment of the present invention, a Fourier transform infrared spectrometer (FTIR) is used.

Figure 2:
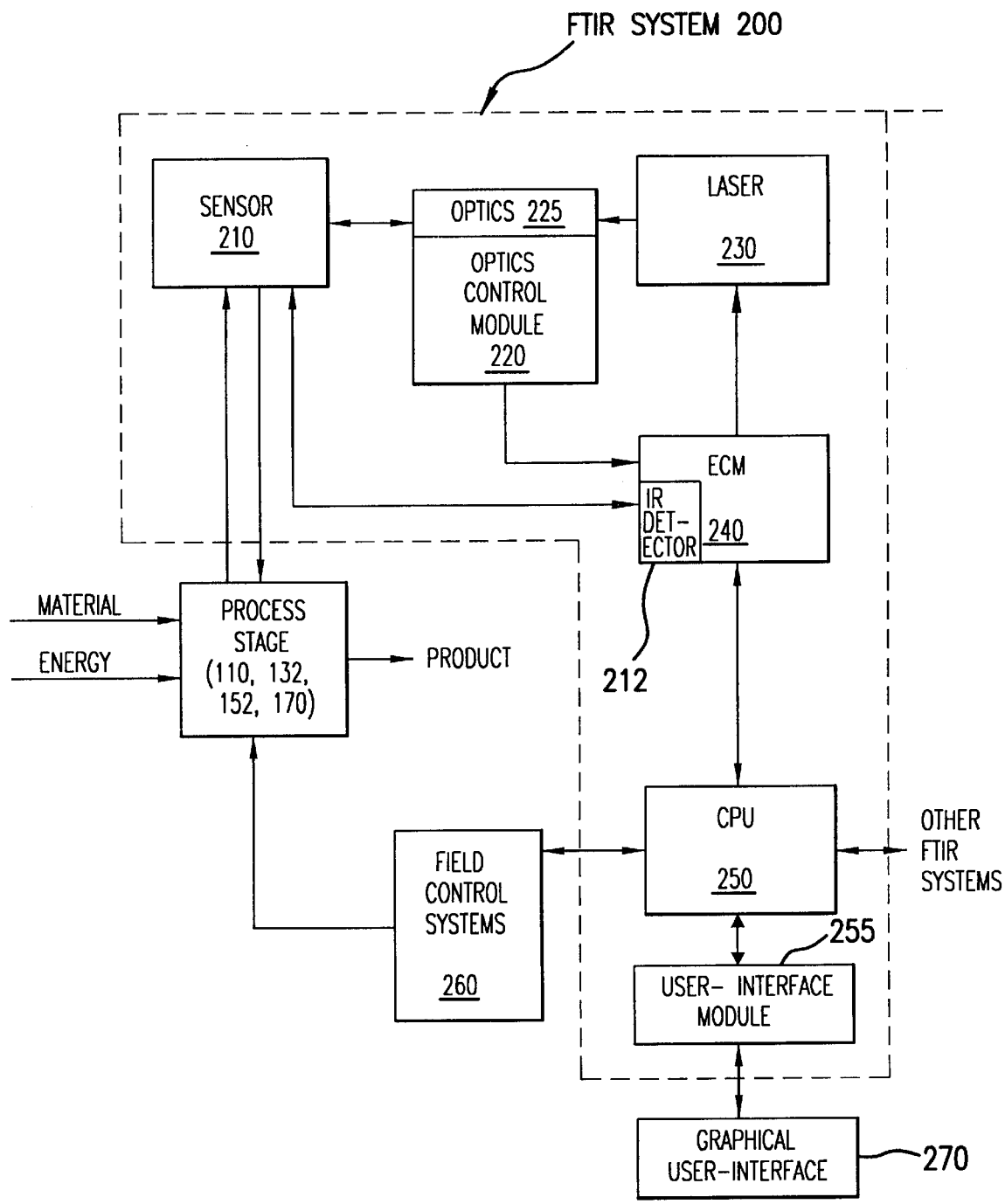
FIG. 2 shows an example FTIR system according to an embodiment of the present invention.

FIG. 2 shows an example FTIR system 200. FTIR system 200 includes a sensor 210, optics control module 220, optics 225, laser 230, electronics control module 240, central processing unit (CPU) 250, and user interface module 255. CPU 250 can be further coupled to field control systems 260 and to other FTIR systems (not shown). Field control systems 260 further control gases, feeds, materials, environmental controls, and other inputs to any one of the stages in biomanufacturing process 100, including bioproduction stage 110, recovery stage 132, purification stage 152, and bulk storage stage 170. CPU 250 can further receive and send data with a graphical user interface to 270 through user interface module 255. Graphical user interface 270 can be any type of graphical user interface including but not limited to a computer monitor, mouse, keyboard, or other input/output device.

In one preferred example, FTIR system 200 can be a ReactIR™ reaction analysis system sold by Applied Systems, Inc. a corporation in Maryland. See, User's Guide, React IR™ and React IR MP™ Mobile Reaction Analysis Systems, $3^{rd}$ Ed., ASI, Applied Systems, Millersville, Md. 1997 (incorporated in its entirety herein by reference). Other systems include, for example, an FTS-6000 system, available from Bio-Rad Laboratories, Hercules, Calif., a Chem-Eye System available from Orbital Sciences, Corp., Dulles, Va., a Foss IR/NIR system, available from Foss North America, Inc., Eden Prairie, Minn., and a Magna-IR 550 Spectrophotometer available from Nicolet Instrument Corp., Madison, Wis. These examples of FTIR systems are illustrative and are not intended to limit the present invention. Other FTIR systems can be used as would be apparent to a person skilled in the art given the description herein.

Laser 230 emits an infrared beam through optics 225 and sensor 210 to the biomolecules in a process stage (bioproduction 110, recovery 132, purification 152, or bulk storage 170). Optics control module 220 controls components and optics 225. For example, optics control module 220 can control focusing, shutters, and any other optical mechanical function. Electronics control module 240 controls the operation of laser 230. CPU 250 coordinates with electronics control module 240 and optics control module 220 to control irradiation of the biomolecules being monitored.

Chemical bonds absorb infrared energy at specific frequencies (or wavelengths). The structure of compounds can be determined by the spectral locations of infrared absorption. The plot of a compound's infrared transmission versus frequency is called a fingerprint. This fingerprint when compared to reference spectra identifies the biomolecule. As would be apparent to a person skilled in the art given this description, the FTIR system 200 mechanically transforms the IR beam into the time domain before the IR beam passes from sensor 210 to a biomolecule in a process stage. Radiation transmitted from sensor 210 through the biomaterial is detected at an infra-red detector 212. Such an infra-red detector 212 can include but is not limited to a mercury cadmium telluride (MCT) detector or a dueturated triglycine sulfate (DTGS) detector. IR detector 212 can be located near sensor 210 or as part of ECM 240. IR detector 212 transduces the infrared beam which passed through, or reflected from, the biosample into an electrical signal which is provided to CPU 250. CPU 250 mathematically transforms the detected signal representing an interferogram into the wave number domain in the form of a single beam spectrum.

The processing of FTIR measurements in stages 110, 132, 152, and 170, the generation of FTIR analyzer reports 120, 140, 160, and 180, and the subsequent generation of appropriate control signals in steps 125, 145, 165, and 185 can be carried out in CPU 250. CPU 250 can be any type of computer, including but not limited to, the example computer system described below with respect to FIG. 8.

A user can provide further control of the bioprocess through graphical user interface 270. In addition to conventional bioprocess controls, additional controls for setting and performing FTIR measurements in each stage 110, 132, 152, and 170 can be provided by graphical user interface 270. For example, buttons, sliders, dial wheels, text fields, pull down menus, or other inputs can be provided at graphical user interface 270 to control the bioprocess in response to real time FTIR measurements.

B. IR Spectroscopic Fingerprinting of a Biomolecule

Figure 3:
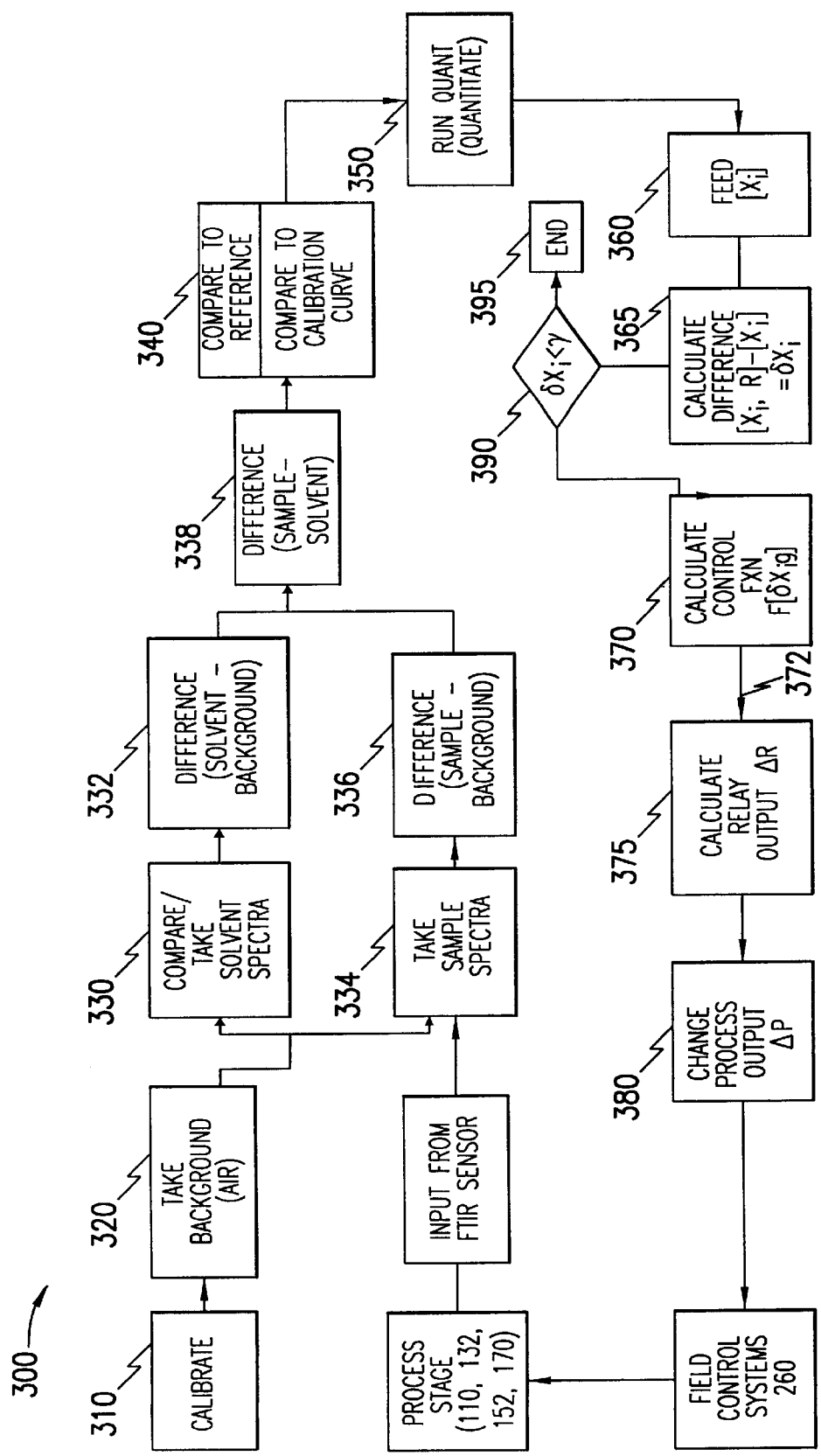
FIG. 3 shows an example routine for identifying a characteristic of a biomolecule according to an embodiment of the present invention.

FIG. 3 shows an example routine 300 for providing FTIR-based control at a biomanufacturing stage according to the present invention (steps 310–380). Steps 310 to 370 relate to the processing of an FTIR measurement and the generation of a corresponding control signal 372. Steps 375 and 380 are one example of providing control to the biomanufacturing stage in response to the control signal 372. This example control system is illustrative. Other types of control systems involving one or more control signals generated in response to FTIR measurement would be apparent to a person of skill given this description. Routine 300 can be provided at the biomanufacturing stages 110, 132, 152, 170 having FTIR-based control as described herein. In the interest of brevity, each of these steps is described in further detail below within an example of the routine 300 as applied to an exemplary step in the recovery stage, e.g., a refolding step 132, and FTIR system 200.

In step 310, calibration of FTIR system 200 is performed. Calibration involves, among other things, generating reference infra-red spectra at various concentrations of the sample and solvent used in refolding step 132. A calibration curve is generated. Calibration step 310 can be initiated manually or automatically prior to and during refolding step 132. An operator can initiate calibration manually through graphical user-interface 270. FTIR system 200 (e.g., CPU 250) can initiate calibration automatically at periodic intervals and/or at selected times during refolding step 132.

FTIR measurement of a biomolecule in real-time during refolding step 132 then begins. An infra-red spectra of the background (e.g., air) is measured (also called taken) (step 320). An infra-red spectra of the solvent is taken (step 330). Note an infra-red spectra of the solvent may be previously stored. In step 332, the background spectra taken in step 320 is subtracted from the solvent spectra taken in step 330 to obtain a first difference output representing the solvent spectra only.

An infra-red spectra of a sample (this includes the biomolecule in refolding step 132) is also taken (step 334), based on the input received from the FTIR sensor (that is, the electric signal(s) output from IR detector 212). The initial measured sample spectra, however, includes solvent and background spectra information. In step 336, the background spectra taken in step 320 is subtracted from the sample spectra taken in step 334 to obtain a second difference output. The first and second difference outputs of steps 332 and 336 are then subtracted to obtain an infra-red spectra of the biomolecule (step 338).

This biomolecule spectra is compared to a reference to determine whether an active biomolecule in refolding step is present (step 340). The biomolecule spectra is also compared to a calibration curve to further verify the validity of the detected biomolecule spectra (step 350). For example, any curve fitting routine can be used in comparison step 350.

Next, optional quantitative information [$x_i$] on the amount of a biomolecule at a certain concentration of solvent can also be obtained from the detected biomolecule spectra. Any conventional FTIR routine that correlates the intensity of a detected infra-red spectra with concentration can be used. Such a routine can be based on a relationship such as Bier's law and/or calibration data relating to the various spectra at known concentrations.

In step 360, the amount of the biomolecule [$x_i$] determined in step 350 is then fed to a process model. The process model determines an [$x_i$,R] value representing what the amount of biomolecule should be at the current time (that is, at the time in which the FTIR measurement and control is being made), and a gamma ($\gamma$) value representing what degree of tolerance is allowed before feedback control is undertaken.

A difference ($\delta$) between the amount of the biomolecule [$x_i$] determined in step 350 and the [$x_i$,R] value output from step 360 is obtained (step 365). In step 390, the difference delta ($\delta x_i$) is compared to $\gamma$. If the difference $\delta x_i$ is less than $\gamma$ (indicating the amount of biomolecule is within an acceptable tolerance), the routine ends (that is, no feedback control action is taken at this iteration (step 395). On the other hand, if the difference $\delta x_i$ is equal to or greater than the gamma (indicating the amount of biomolecule is not within an acceptable tolerance) then data 372 representing the amount of control to be applied is generated (step 370). In one example, the difference $\delta x_i$ and $\gamma$ values are input to a function to determine the amount of control data 372. In this way, the degree of the control response for refolding stage 132 can be based upon the value of the $\gamma$ for a particular process model and the amount of the difference $\delta x_i$.

The amount of control data 372 is then translated into an appropriate control signal depending upon the particular components used in regulating refolding stage 132. For example, in step 375, a relay adjustment signal (delta R) is determined as function of the amount of control data 372. The relay adjustment signal can then be added to a relay control of a relay (not shown) to adjust the control of air fed from an air pump (not shown) to refolding step 132.

The amount of control data 372 can also be used to generate a process control signal (delta p) (step 380). This process control signal can be used for other process control adjustments in refolding stage 132.

Figure 4:
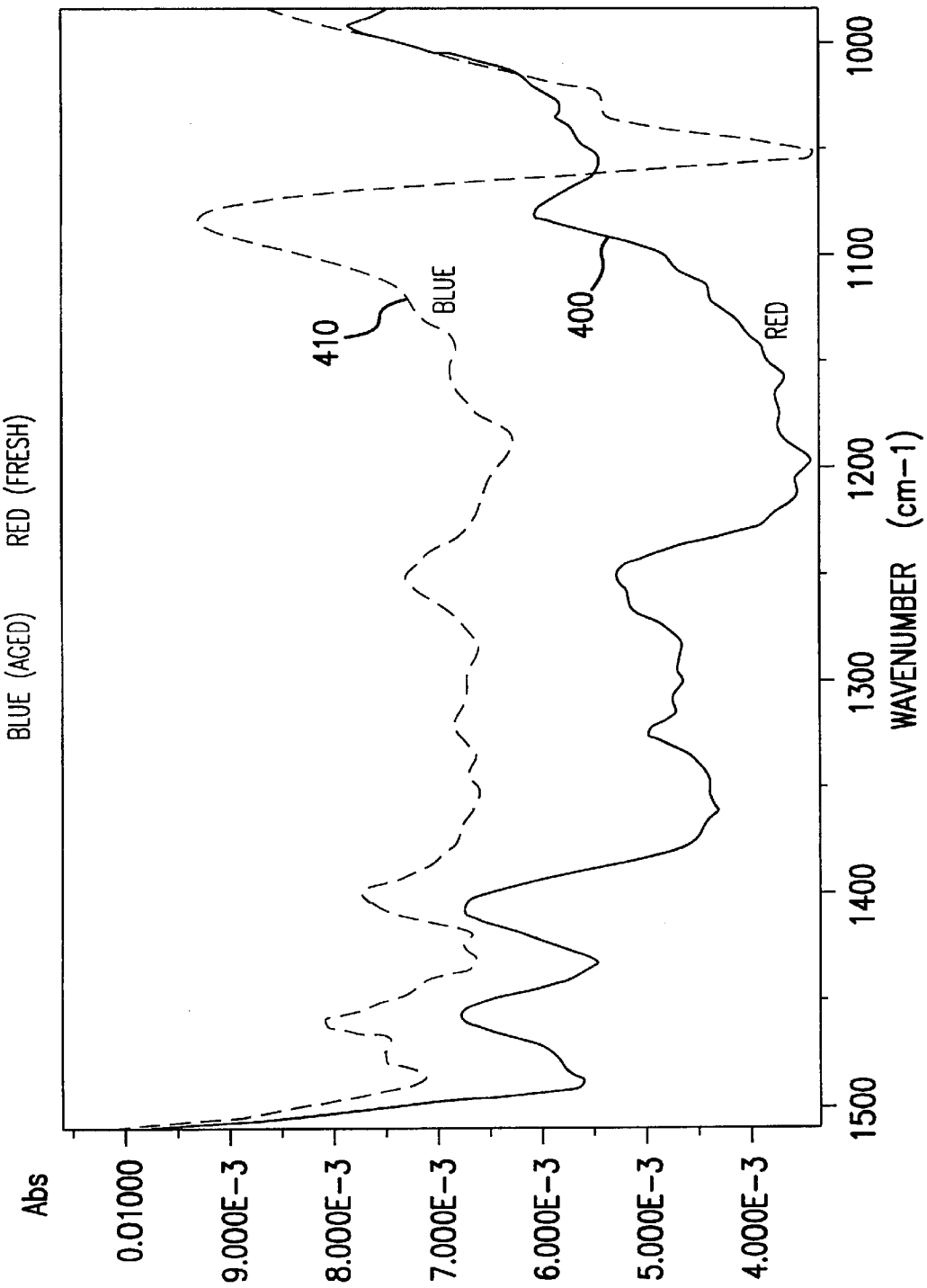
FIG. 4 is a diagram of that illustrates differences in FTIR spectra between aged and fresh biomolecule samples.

FIG. 4 shows an example of a measured spectra 410 obtained for an inactive species of a biomolecule. This spectra includes wave numbers between 1,500 and 1000 cm$^{-1}$. This spectra 410 is represented by a plot of absolute units of transmission or radiation intensity ranging from $4.000 \times 10^{-3}$ to $0.01000$ over the range of wave numbers between 1,500 and 1000 cm$^{-1}$. A spectra of a representative pharmacologically active biomolecule is represented by the spectral plot 400. As shown in FIG. 3, the difference between spectra 410 and spectra 400 is calculated in step 365. In particular the absolute values of the measured spectra 410 can be compared to the spectra 400 for wave numbers between 1,500 and 1,000 cm$^{-1}$, and preferably between wave numbers 1400 and 1100 cm$^{-1}$. Based on this comparison, if the spectra 410 is within a previously determined conformance with spectra 400 (i.e.,$\delta x_i < \gamma$), the process step proceeds to its endpoint 395. If, on the other hand, the spectra 410 is not in the desired conformance with spectra 400 (i.e., $\delta xi \geq \gamma$), the control steps are initiated (370, 375, and 380).

III. Real Time Process Control in Bioproduction

The present invention provides real-time process control for optimal bioproduction as a first step in the biomanufacturing process. As used herein, "bioproduction" refers to any way in which a biomolecule may be formed, modified, synthesized, or replicated. Examples of bioproduction include, but are not limited to, the following. In one preferred embodiment, bioproduction includes synthesis of proteins, nucleic acid molecules, or organic metabolites by viruses, e.g., animal viruses, plant viruses, or bacteriophages, or living cells, e.g., bacterial cells, yeast cells, insect cells, or higher eukaryotic cells. Examples of modifications include, but are not limited to methylation, demethylation, deamination, or ex vivo glycosylation. This form of bioproduction normally is carried out in a controlled system, for example in a fermentation, in culture flasks, or in a bioreactor. Often, the biomolecule is expressed by a heterologous gene in an expression system. Suitable expression systems are well known to those skilled in the art and include, but are not limited to: bacterial expression, especially expression in *Escherichia coli;* mammalian cell expression systems, for example, expression in chinese hamster ovary (Cho) cells, Cos cells, HeLa cells, 3T3 cells, BHK-21 cells, or Vero cells; insect cell expression systems, especially the baculovirus expresion system using Spodoptera sp. and *Trichoplusia ni* cells; yeast cell expression systems, especially expression in *Saccharomyces cerevisiae* and *Pichia pastoris;* and virus expression systems, including poxvirus, Sindbis virus, herpesvirus, adenovirus, retrovirus, and picornavirus expression systems. Another embodiment of bioproduction includes semi-synthetic processing of biomolecules. Examples include, but are not limited to: peptide synthesis; oligonucleotide synthesis; additions to biomolecules such as carboxylation, lipidation or pegolation; catabolic processes such as peptide cleavage, deglycosylation, removal of lipids, or restriction digestion of polynucleotides; and refolding or reprocessing of a biomolecule.

Yet another embodiment of bioproduction includes extractive processes to obtain biomolecules from plants, animals, and embryos, both native and transgenic. Examples include, but are not limited to, isolation of biomolecules from blood, ascites, lymph, urine, seminal fluid, milk, chloroplasts, sap, bark, and chorionic fluid. Yet another embodiment ofbioproduction includes the production of therapeutic viruses, for example, killed and/or modified live viral vaccines, viral vectored vaccines and gene therapy delivery vehicles. Examples include, but are not limited to, production of conventional vaccines, including, but not limited to smallpox vaccines (e.g., vaccinia virus), measles vaccines, rubella vaccines, varicella vaccines, influenza vaccines, rabies vaccines, hepatitis vaccines, and rotavirus vaccines; and production of novel recombinant viral vectored vaccines and gene therapy delivery vehicles in vectors including, but not limited to poxviruses, herpesviruses, adenoviruses, retroviruses, picornaviruses, and alphaviruses. Large scale bioproduction of therapeutic viruses is carried out either in a tissue culture system, e.g., in a bioreactor, or in an in vivo host, e.g., in embryonated chicken eggs, milk, urinary tract, endothelial cells, or epithelial cells.

Bioproduction of antibodies is carried out by any suitable method known in the art. For example, a polypeptide biomolecule or an antigenic fragment thereof can be administered to an animal in order to induce the production of sera containing polyclonal antibodies. Monoclonal antibodies can be produced using a wide variety of techniques known in the art including the use of hybridoma, recombinant, and phage display technology. Hybridoma bioproduction methods include those known in the art and taught in Harlow et al., *Antibodies: a Laboratory Manual,* (Cold Spring Harbor Laboratory Press, 2nd ed. 1988); Hammerling et al., in: *Monoclonal Antibodies and T-cell Hybridomas* 563–681 (Elsevier, N.Y., 1981) (said references incorporated by reference in their entireties).

A preferred bioproduction process of the present invention is fermentation, i.e., the controlled growth of a cell culture to high yield. As used herein, "fermentation" refers to the controlled culture of any type of living cell, including bacterial cells; yeast cells; fungal cells; animal cells, including insect cells, bird cells, fish cells, mammalian cells (including human cells); and plant cells. By "controlled growth" it is meant that the entire environment with which a cell is contacted is controlled, to the extent possible, by the operator of the fermentation. For example, a fermentation will have controlled temperature, pH, oxygen and carbon dioxide concentration, agitation, and nutrients.

Examples of bioproduction procedures, including fermentations, may be found, for example, in *Current Protocols in Protein Science,* Coligan et al., eds., John Wiley and Sons, Inc. (1997), which is incorporated herein by reference in its entirety.

An example of a fermentation of the present invention would be growth of a culture of a recombinant bacteria, for example, a culture of recombinant *Escherichia coli,* which has been genetically engineered to produce a biomolecule, for example, human interleukin-10 (hIL-10). Other examples might include a culture of recombinant eukaryotic cells, for example, Cho cells, which have been genetically engineered to produce a biomolecule, for example, tissue plasminogen activator, or culture of yeast cells, for example *Saccaromyces cerevisiae* or *Pichia pastoris.*

During a fermentation, one main goal of real-time IR monitoring and feedback control is to maintain homeostasis, for example, extracellular and intracellular homeostasis, which is an indirect control for optimization of the yield and quality of biomolecule production. As a secondary goal during bioproduction, real-time IR monitoring is used to optimize the yield of cell mass, and the yield of the pharmacologically active form of the biomolecule.

The present invention provides several points at which real-time IR monitoring and feedback control of bioproduction may be accomplished. These points may be divided among those that are utilized for production of a biomolecule that remains intracellular throughout the bioproduction stage (points (a) through (d)), and those that are utilized for production of a biomolecule that is secreted into the medium during bioproduction (points (a) through (e)). These monitoring points include, but are not limited to, (a) measurement and control of nutrient concentrations to maintain real-time homeostasis in the fermentation reactor, (b) measurement of the concentration of soluble metabolic by-products as a correlate for estimated biomass yield of the fermentation, (c) direct quantification and control of dissolved gases in the fermentation, (d) monitoring and control of a shift from conditions optimal for cell growth to conditions optimal for biomolecule synthesis (e.g., "induction"), and (e) real time monitoring, by "fingerprinting," of the proportion of the pharmacologically active form of a biomolecule relative to inactive forms, with immediate and appropriate adjustments of the conditions of the bioproduction process in order to optimize the yield of the pharmacologically active form of the biomolecule. Specific examples of bioproduction monitoring and control using IR are provided herein.

Which applications of IR monitoring and control of bioproduction used in any given biomanufacturing process largely depend on the type of bioproduction that is being used. In some fermentations, the biomolecule of interest may be synthesized by the cultured cell and remain intracellular throughout the bioproduction stage. For example, the biomolecule may remain in the cytoplasm of the cultured cell, or it may be transported to a compartment of a cell, for example, the periplasmic space of a gram-negative bacteria, or an inclusion body of a bacteria or a eukaryotic cell. As used herein, an "inclusion body" is an insoluble protein aggregate produced by a microorganism or other host cell. In such a situation, the biomolecule of interest would not be detectable itself by IR monitoring, and thus, production of the biomolecule is optimized by correlating, in real time, other parameters of the fermentation, thereby providing an estimate of the ideal conditions for production of the biomolecule. In order to measure these parameters, an IR probe is inserted directly into a fermentation reactor, and then is connected to computer and user interfaces, to provide immediate feedback controls during the fermentation.

Figure 5:
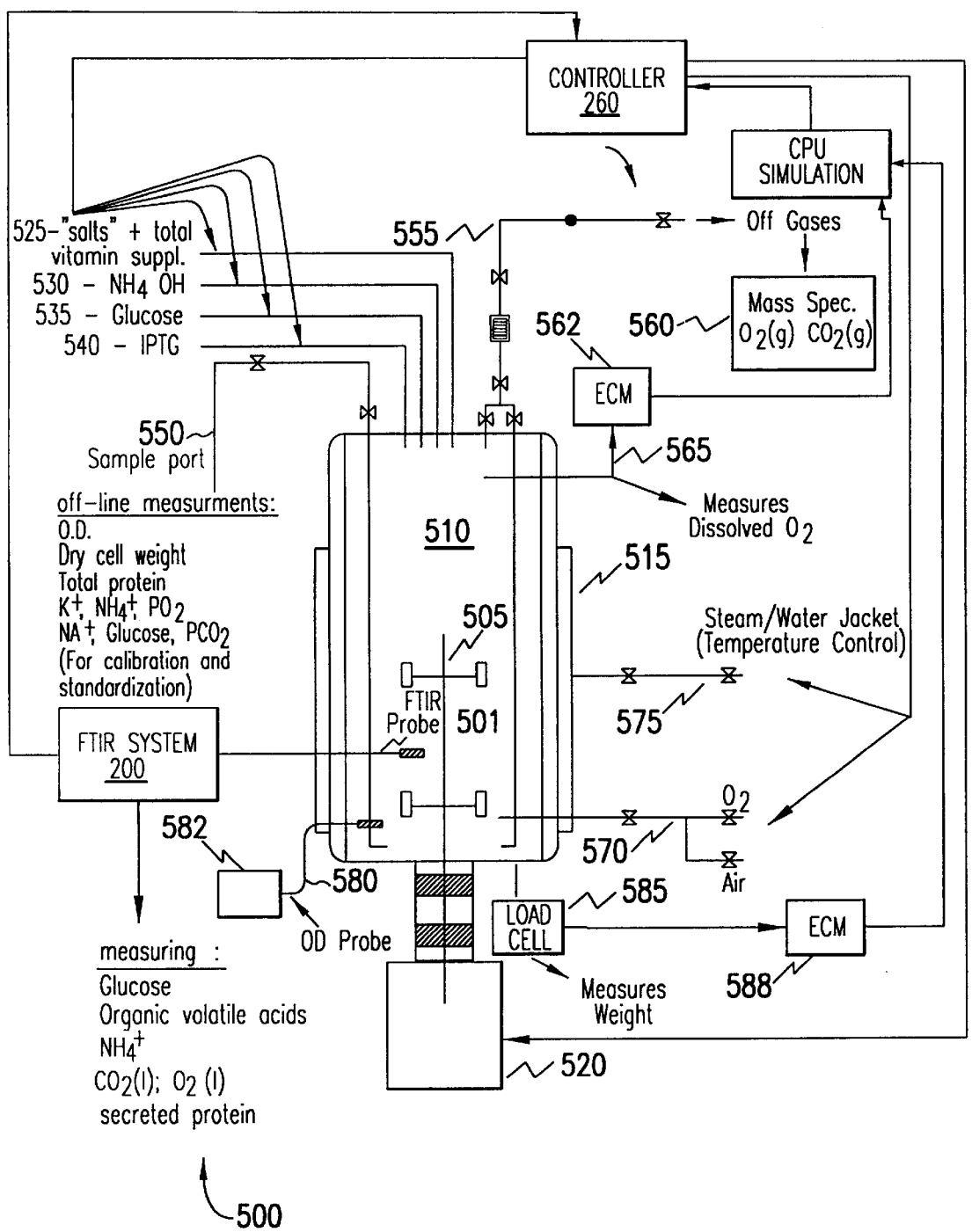
FIG. 5 is a diagram of a fermentation reactor of the present invention, showing monitoring by FTIR and feedback control of the fermentation process.

FIG. 5 shows an example of a fermentation system 500 with real time process monitoring and control using IR. Fermentation reactor 510 is installed with impeller 505 driven by motor 520. The fermentation reaction is run with a standard culture medium, for example LB medium, or a defined culture medium. Suitable culture media may be found, for example, in Coligan et al., ibid., at pages 5.3.12 to 5.3.14. In order to measure appropriate parameters, the bioproduction process is monitored, in the range of wave numbers from about 5000 to 300 cm$^{-1}$, preferably at a range of wave numbers from about 4000 to 500 cm$^{-1}$, and more preferably in ranges of wave numbers from about 4000 to 2200 cm$^{-1}$ and from about 1900 to about 700 cm$^{-1}$, using a probe 501, such as a probe to an FTIR system 200, inserted into the fermentation reactor 510. Examples of parameters to measure include, but are not limited to, substrate concentration, e.g., glucose or other carbohydrate present in the fermentation medium; direct quantification of organic volatile acids such as acetate, pyruvate, and lactate, which may be used as a correlate for estimated yield of the fermentation, i.e., accumulation of cell mass; accumulation or depletion of free amino acids or their salts, direct quantification of dissolved gases in the fermentation reaction, for example, quantification of oxygen ($O_2$) or carbon dioxide ($CO_2$); and direct quantification of ammonium ion ($NH_4^-$). Characteristic IR absorption characteristics of various medium components and metabolites, may be found, e.g., in Doak and Phillips, *Biotechnol. Prog.* 15(3):529–39 (May/June1999), which is incorporated herein by reference.

Based on these real-time measurements of the fermentation conditions, immediate feedback control is provided to maintain homeostasis in the fermentation reactor, and secondarily, through, e.g., parametric modeling, to optimize high yield production of the pharmacologically active form of the biomolecule, with adjustments being made, e.g., to the glucose feed 535, salts and total vitamin supplement feed 525, amonium hydroxide feed 530 air/$O_2$ feed 570, temperature 575, and agitation and aeration by impeller 505 and gas flow 570.

In order to correlate a given IR spectrum with optimal bioproduction conditions, other measurements are taken during the fermentation reaction. These include (a) mass spectroscopy 560 of off-gases 555 ($O_2$ and $CO_2$) to combine with direct FTIR measurement of dissolved $O_2$ and $CO_2$ to calculate the mass balance of the fermentation, (b) measurement of the optical density (OD) of the fermentation culture at about 600 nm by detector probe 580 connected to an electronic control module (ECM) 582, (c) a probe for measurement of dissolved $O_2$ 565 connected to an ECM 562, (d) a load cell 585 to measure the weight of the fermentation culture connected to an ECM 588, and (e) off-line measurements, from a sample taken at port 550 of OD, dry cell weight, total protein, K+, Na+, $PO_2$, $PCO_2$, $NH_4^+$, and glucose, for standardization and calibration. ECMs 582, 562, and 588 are connected in line to a CPU simulation, which also feeds back information to controller 260.

In one embodiment, a fermentation with IR monitoring and control is run with two or more sets of reaction conditions as the fermentation progresses. For example, it may be desirable to start the fermentation with conditions, as in FIG. 5, to optimize the production of cell mass, and then when such an optimal point is achieved, to shift to fermentation conditions which are optimal for production of the biomolecule. According to the present invention, IR monitoring and control is used determine the optimal point in the fermentation to shift from the first set of conditions, for example, conditions that optimize production of cell mass, to the second set of conditions, for example, conditions that optimize biomolecule production. This shift in conditions is referred to herein as an "induction" of the fermentation culture. Methods of induction are well-known to those skilled in the art and may be found, for example, in Coligan et al., ibid. at p. 5.2.2 to p. 5.2.5. Induction can include, for example, raising the temperature of the fermentation, e.g., with the cI857 repressor/$p_L$ system, or by the addition of one or more chemical compounds, e.g., isopropyl-thiogalactoside (IPTG) with the lac/tac system, or indole-3-acrylic acid (IAA) with the trp system, to the fermentation to induce protein synthesis. In this way, the present invention provides manual or automated control of the induction process. When predetermined optimal conditions in the fermentation reaction are detected through use of IR, induction of the culture occurs through immediate feedback control, for example by IPTG feed at port 540.

In other bioproduction processes, a biomolecule may be synthesized and lodged in the surface of the cell, e.g., in the cell wall or in the cell membrane of a cultured cell, such that a portion of the molecule may be exposed to the culture medium, and a portion remains intracellular or inside the cell wall or cell membrane. Alternatively, a biomolecule may be synthesized by the cultured cell and then be fully secreted or excreted during the bioproduction stage, i.e., released as a soluble biomolecule into the culture medium. In these situations, in addition to the IR monitoring and control points described above, the "fingerprint" of the biomolecule itself is monitored, for example, to detect the level of production of the pharmacologically active species of the biomolecule, or to detect, over the time of the bioproduction, the level of degradation or biosynthetic conformational variation of the biomolecule as it is released from the cultured cells. As described above, in response to real-time IR measurements of the biomolecule, conditions of a fermentation reaction may be adjusted, e.g., temperature or nutrient components may be immediately altered, or the fermentation may be terminated, to optimize quantity and quality production of the pharmacologically active form of the biomolecule.

IV. Real Time Process Control in Recovery

Figure 6:
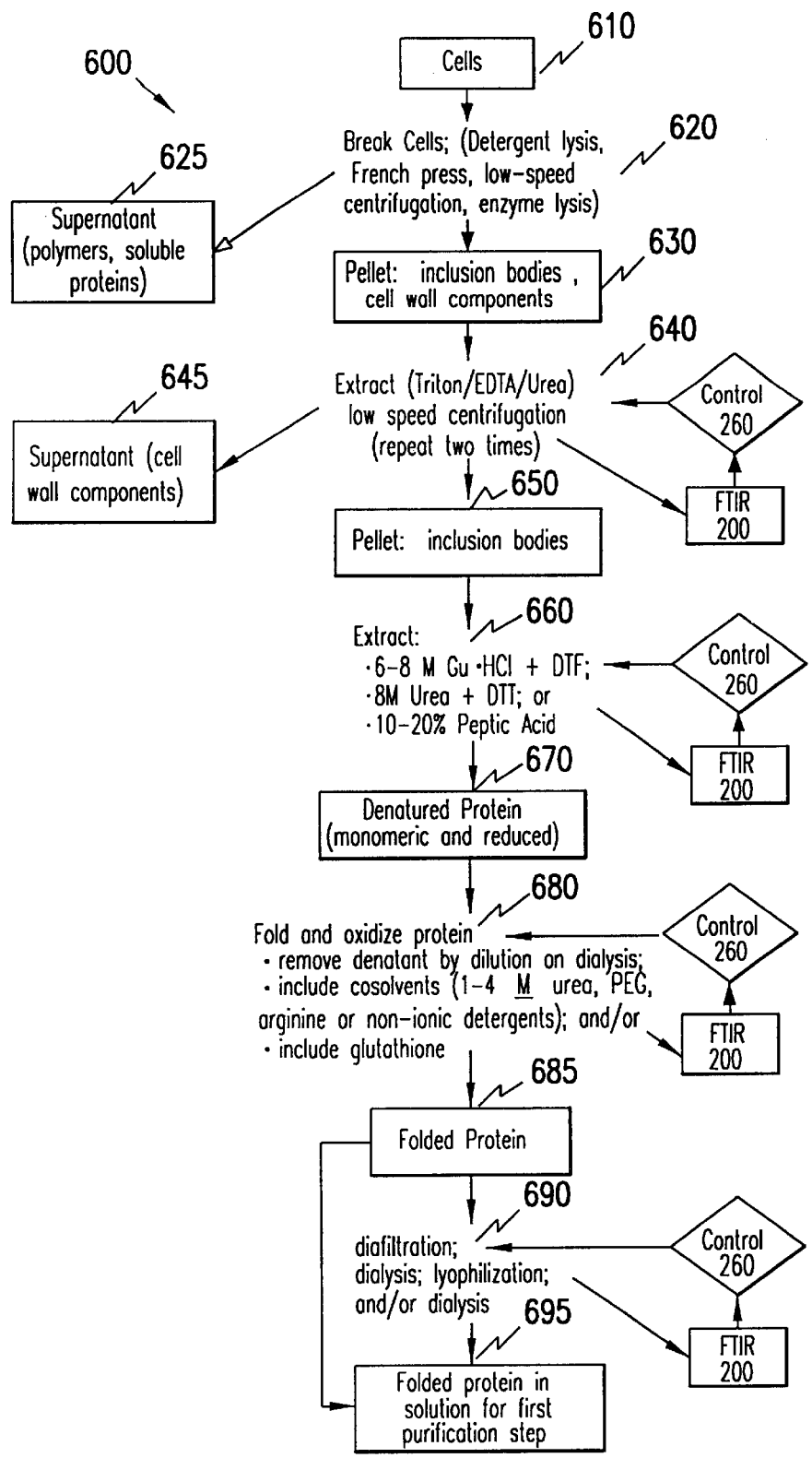
FIG. 6 shows a flow diagram of a recovery process in a biomolecule manufacture with FTIR monitoring and control points.

FIG. 6 shows a flow diagram of a recovery process in a biomolecule manufacture with FTIR monitoring and control points. As used herein, "recovery" in a biomanufacturing process refers to steps of the process after bioproduction or fermentation, including, but not limited to (a) a solid/liquid separation step for recovery of cells containing the biomolecule, or, alternatively, separation of cells from the culture medium containing a secreted biomolecule, e.g., by centrifugation or microfiltration skid (resulting in cells, 610), (b) lysis or breakage of cells to release the biomolecule (620), (c) recovery of inclusion bodies by centrifugation followed by extraction of the biomolecule from the inclusion bodies (630, 640, 660, and 670), (d) removal of gross particulates from the biomolecule mixture (e.g., 650), (e) initial gross physical separations (e.g., precipitation or extraction) of the biomolecule from other components, (f) renaturation or refolding of denatured biomolecules (680), (g) diafiltration or lyophilization steps to alter and/or change the solution in contact with the biomolecule (690), and (h) passage through a micro-filter prior to purification. Methods of performing these steps are well known to those skilled in the art, and are disclosed, for example, in Coligan et al., ibid. Additional methods of refolding or renaturing proteins may be found, for example, in U.S. Pat. Nos. 5,808,006; 5,756,672; 5,750,361; and 5,739,281; in Ejima et al., *Biotechnol and Bioeng.*, 62:301–310 (February 1999); and in Batas et al., J. Biotechnol. 68:149–158 (February 1999), all of which are incorporated by reference.

Which steps are used in any given recovery process depends largely on the type of bioproduction process used and the nature of the biomolecule being manufactured. One skilled in the art, given this description, would readily know which steps to use based on the conditions of the biomanufacturing process. Appropriate steps for various biomanufacturing recovery processes are disclosed, for example in Coligan et al., ibid. at chapters 5 and 6.

According to the present invention, recovery steps at which IR spectroscopic monitoring and feedback control are used include, but are not limited to, lysis 620, precipitation, lyophilization 690, diafiltration 690, and/or refolding or renaturation 680. In some embodiments, IR spectroscopic monitoring is further utilized between the other recovery steps to assess the activity of the biomolecule prior to the next step.

In the recovery stage of biomanufacturing, IR spectroscopic monitoring is used to monitor the biomolecule of interest, both quantitatively and qualitatively, and immediate controls are provided to optimize the recovery process for maximum yield of the pharmacologically active form of the biomolecule. For purpose of illustration FIG. 6 depicts an example recovery process for a protein biomolecule contained in *E. coli* inclusion bodies. A recovery process is described in greater detail in Example 1, infra.

At certain recovery steps, an IR probe, such as, a probe to an FTIR system, is contained in a flow cell attached in-line to the process stream. IR measurements are taken by running the recovery process through flow cells and measuring the biomolecule at a range of wave numbers from about 300 to 5000 $cm^{-1}$. During lysis, IR spectroscopic monitoring is used to measure the relative ratios of species of the biomolecule, for example, the ratio of active to inactive, the ratio of native to denatured, or the ratio of species with alternative forms of disulfide bonding. During precipitation, IR spectroscopic monitoring is used to measure the removal of nucleotides, and the effects of the precipitation on the quality of the biomolecule, similar to the use during the lysis step. During diafiltration, IR spectroscopic monitoring is used to monitor the effect of shear forces and pressure, e.g., transmembrane pressure, on the biomolecule. During lyophilization, IR spectroscopic monitoring is used to monitor the effect of cooling and vacuum on the biomolecule. During renaturation, IR spectroscopic monitoring is used to monitor the effect of refolding reagents and oxidation on the quality and quantity of the biomolecule.

Based on IR spectroscopic monitoring, immediate feedback controls are provided to maintain the biomolecule in its most pharmacologically active form. These controls include, but are not limited to (a) alteration of the concentration of conformational enhancers including, but not limited to chaotropic agents in the lysis or renaturation buffers (e.g., guanidine HCl, cysteine, dithiothreitol (DTT), or urea) to establish or maintain proper folding of the molecule, (b) controlling refolding of a biomolecule through adjustment of the oxidation conditions by adjustments to the air feed to the reaction, (c) determination of allowable time intervals for the lysis, denaturation, precipitation and renaturation steps to prevent excess denaturation or proteolytic degradation, (d) adjustments in the time and temperature of a precipitation, and (e) slowing or accelerating a diafiltration to adjust shear forces and pressure.

V. Real Time Process Control in Purification

As used herein, "purification" comprises the biomanufacturing steps where the biomolecule of interest is separated from other molecules and purified, essentially to homogeneity. Purification steps may be divided into two groups, physical and chemical. Physical separation techniques include, for example, precipitation, continuous sucrose gradient centrifugation, and filtration. Chemical separation techniques include, for example, chromatography, chemical extraction, and electrophoresis.

Chromatographic separation techniques are well known to those skilled in the art. Examples of chromatographic separations may be found, for example in Coligan et al., ibid., at chapters 8 and 9. These include, but are not limited to, ion (both cation and anion) exchange chromatography, gel filtration chromatography, hydrophobic interaction chromatography, chromatofocusing, hydroxylapatite chromatography, and affinity chromatography. Other methods include reverse phase HPLC, sulfonated carbohydrate chromatography and expanded bed adsorption chromatography, for example, the STREAMLINE System available from Pharmacia Biotech. Each of these categories of chromatography provides a variety of chromatographic media for various uses, as would be readily apparent to the skilled artisan. Types of ion-exchange media may be found, for example, at pages 8.2.5 to 8.2.7 of Coligan,, ibid. Types of gel filtration media may be found, for example, at pages 8.3.2 to 8.3.5 of Coligan, et al., ibid. Types of hydrophobic interaction media may be found, for example, at page 8.4.2 of Coligan et al., ibid. Types of gels for chromatofocusing may be found, for example, at page 8.5.4 of Coligan et al., ibid. Matrices for hydroxylapatite chromatography may be found, for example, at page 8.6.2 of Coligan et al., ibid. Media for various types of affinity chromatography, e.g., lectin affinity chromatography, dye affinity chromatography, affinity chromatography with natural ligands, metal chelate affinity chromatography, immunoaffinity chromatography, DNA binding protein affinity chromatography, or biotin/streptavidin affinity chromatography may be found, for example, throughout chapter 9 of Coligan et al., ibid. The number and type of chromatography steps used in the purification of a biomolecule depend largely on the nature of the biomolecule being purified, the nature of the source material from which it is to be separated, the level of purity required, and the yield required from the purification. An example purification protocol is disclosed for the biomolecule hIL-10 in Example 1, infra.

Figure 7:
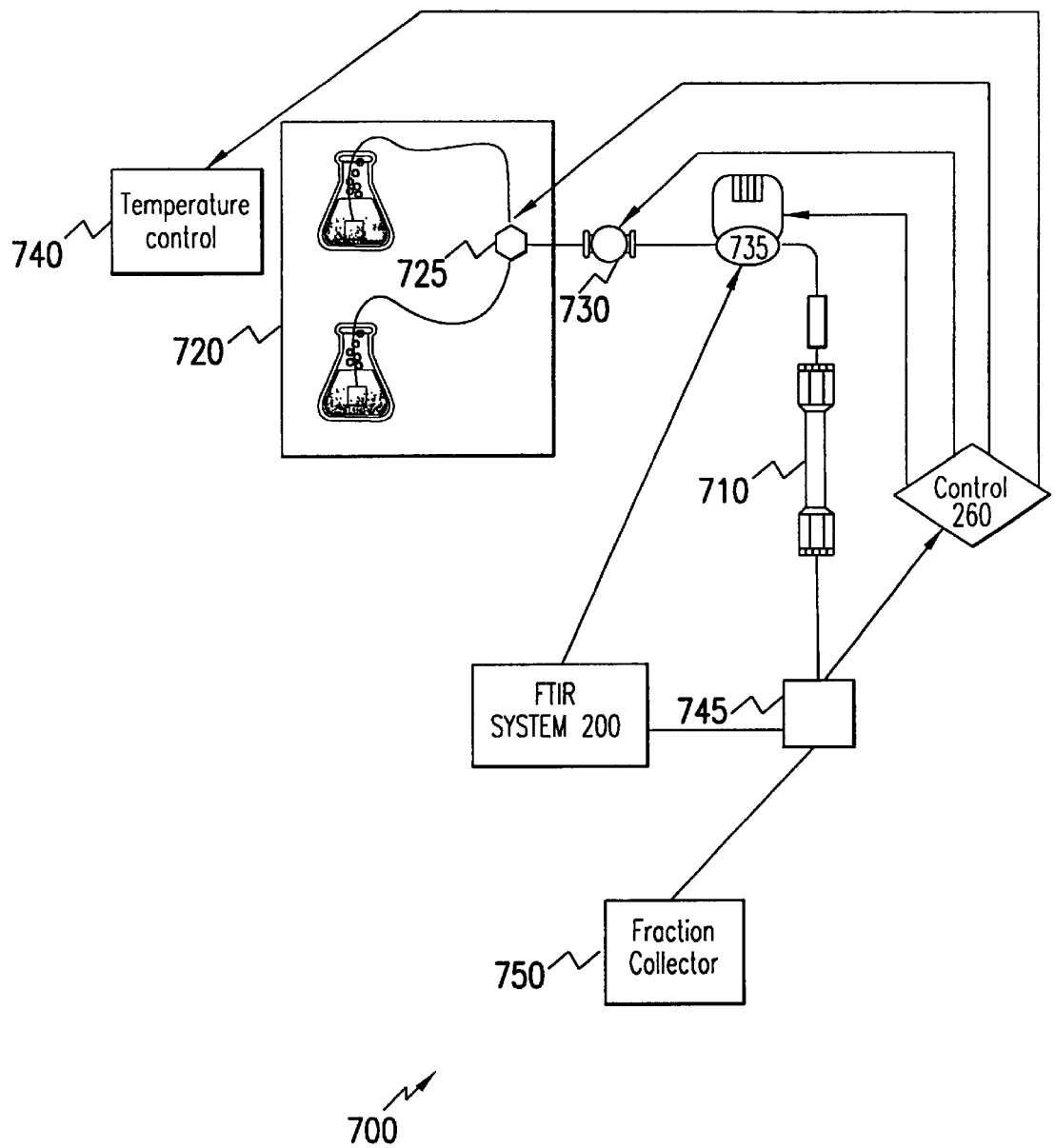
FIG. 7 is a diagram of a chromatographic separation process showing monitoring and control of the process by FTIR.

The present invention provides IR spectroscopic monitoring and feedback control of each chromatography or other purification step to maximize the quantity, pharmacological activity, and purity of the biomolecule of interest. An example of a chromatography system is shown in FIG. 7. This system 700 includes buffer reservoirs and a mixer for gradient formation 720 having temperature control 740, an in-line peristaltic pump 730, a sample injector equipped with an in-line flow cell equipped with an IR probe capable of wave number measurements ranging from about 300 to 5000 $cm^{-1}$ 735 connected to FTIR system 200, a chromatography column packed with the chromatographic resin 710, an in-line flow cell equipped with an IR probe capable of wave number measurements ranging from about 300 to 5000 $cm^{-1}$ 745 connected to FTIR system 200, a computer interface capable of providing feedback controls to the chromatography separation 260, and a fraction collector 750.

Chromatographic separations can be separated into two categories: "retentive" separations, i.e., those where the biomolecule of interest is retained on the chromatography resin and is subsequently eluted, and "extractive" separations, i.e., those where the biomolecule of interest flows through the chromatography resin, while unwanted components are retained on the column. Retentive separations can also use either batch adsorption techniques, i.e., where the absorption takes place in a slurry with the chromatography resin, or by column absorption techniques, i.e., where the adsorption takes place by running a solution containing the biomolecule through a column. In either case of retentive chromatographic separation, the biomolecule of interest is bound to the column resin, e.g., by an ionic, hydrophobic, or affinity interaction. During each chromatographic separation, the solution containing the biomolecule is monitored by IR spectroscopy before and after adsorption, at points 735 and 745, to ensure that the majority of the biomolecule has bound to the column material, thus improving the yield of the purification process. Immediate feedback controls are provided to either alter the rate of the adsorption process at 735 or to solicit user intervention.

Following binding of the biomolecule of interest to the chromatography resin, the biomolecule is eluted from the column. Certain methods of elution allow the skilled artisan to specifically control the point in the elution that the biomolecule of interest is released from the resin. These methods include, but are not limited to, use of a salt gradient, gradually mixing an aqueous buffer with an organic solvent, or the gradual addition of detergents. IR spectroscopy is used to monitor this elution step at point 745 and to provide immediate feedback controls to (a) control the resolution of the elution, i.e., narrow the peak where the biomolecule elutes and improve the separation of the biomolecule from other material bound to the column, and (b) qualitatively maintain the active structure of the biomolecule. Feedback controls include, but are not limited to, adjustment of the elution buffer temperature 740 or pH, adjustment of the salt gradient curve 725, adjustment of the pump speed 730, and adjustment of the elution buffer components 720.

In particular, IR spectroscopic monitoring is used to monitor specific fractions eluting from the chromatography column that contain the biomolecule of interest, allowing the artisan to measure, in real time, the quantity, quality, and pharmacological activity of the biomolecule eluting from the column, and to provide immediate feedback to improve the elution profile. For example, during elution from a column, the conformation of a biomolecule may be altered, either by temperature, the nature of the elution buffer, or the profile of a chemical gradient. The present invention provides immediate feedback controls to adjust the parameters of the elution to maintain the biomolecule in its most pharmacologically active form.

Based on the conditions used, a biomolecule may elute from a column very sharply, i.e., in a small number of fractions, or it may elute more broadly, i.e., in a larger number of fractions. Furthermore, along with the biomolecule of interest, additional material may also bind to the chromatography column. It is often possible for the skilled artisan to adjust the elution conditions to separate the biomolecule of interest from unwanted material during elution, and to sharpen the peak at which the biomolecule elutes. This is referred to as improving the resolution of the chromatography process. The standard method of assessing the resolution of a chromatographic separation is to monitor the elution profile with a UV detector for absorbance at 280 nm, which provides a rough measurement of total protein eluting in a given fraction. However, it is well known that a single peak measured by UV absorbance may contain multiple substances that are not resolved by the particular chromatographic separation technique. As provided by the present invention, IR spectroscopic monitoring, in contrast to measurement of UV absorbance, measures the fingerprint of the specific biomolecule of interest, and allows for immediate feedback control of the elution profile to sharpen the resolution, thus markedly improving the quality of the purification relative to existing techniques.

VI. Real Time Process Control in Bulk Formulation and Storage

Following purification of a biomolecule, the manufacturing process includes formulation and storage steps. Formulation includes resuspending the biomolecule in a final solution containing physiologically acceptable excipients and carriers and/or lyophilizing the biomolecule formulation, aseptically processing the formulation, and finally, storing the biomolecule formulation in bulk, awaiting finish and fill processes. During bulk storage, it is imperative to know that a biomolecule formulation, after a certain amount of storage time, retains its activity, and to assess the specific activity of the formulation after long-term storage.

The present invention provides for real time, in situ IR monitoring of a biomolecule stored in bulk, and provides feedback controls to maintain optimal conditions for storage of the biomolecule. Thus, the present invention solves many problems associated with bulk storage and stability studies. Rather than extrapolating the stability of a biomolecule over time, the skilled artisan can interpolate the stability based on actual data.

A. Real-Time Monitoring and Control Including FTIR

Figure 9:
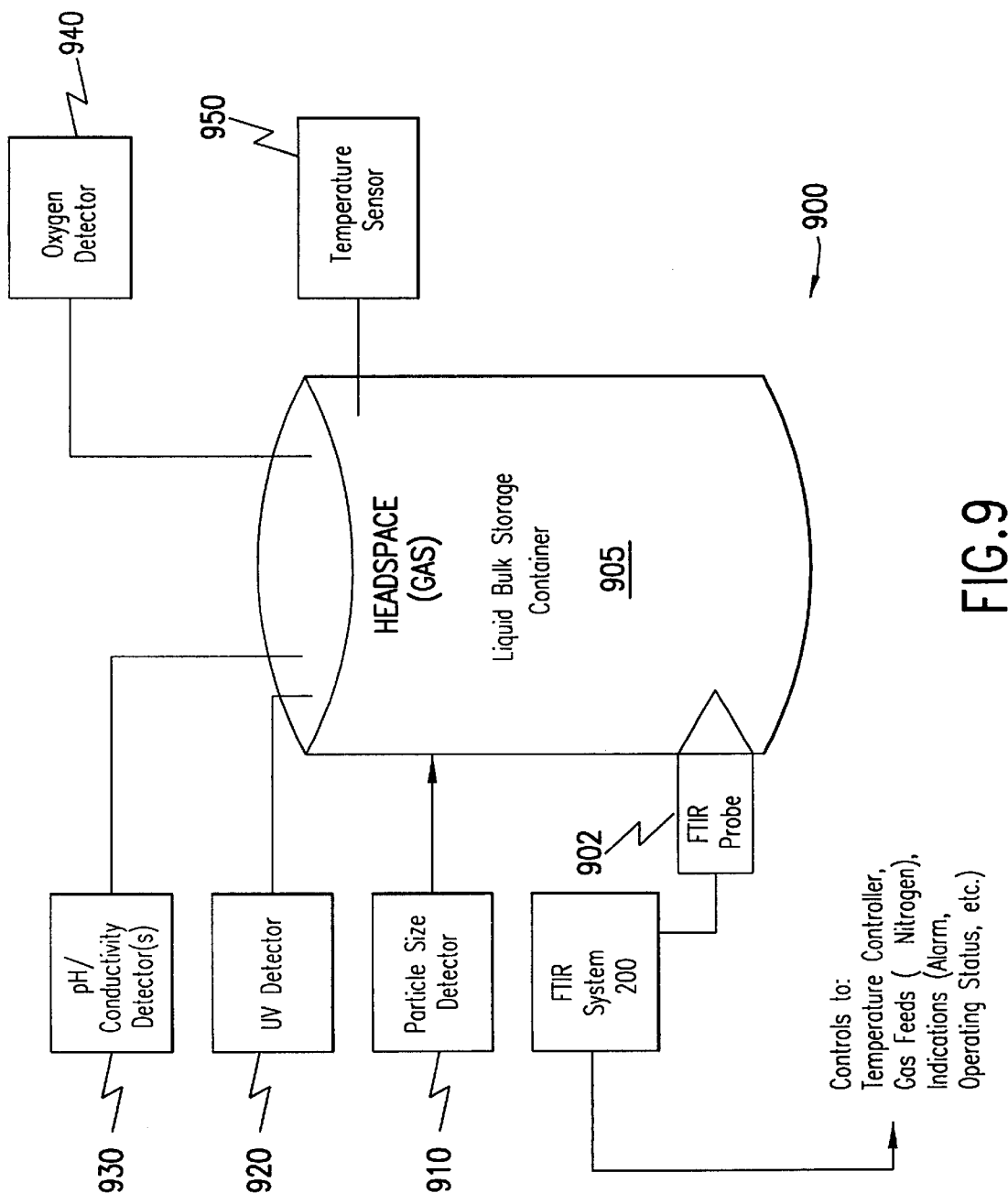
FIG. 9 is a diagram of a real-time bulk storage monitoring system including FTIR monitoring and control according to an embodiment of the present invention.
Figure 10:
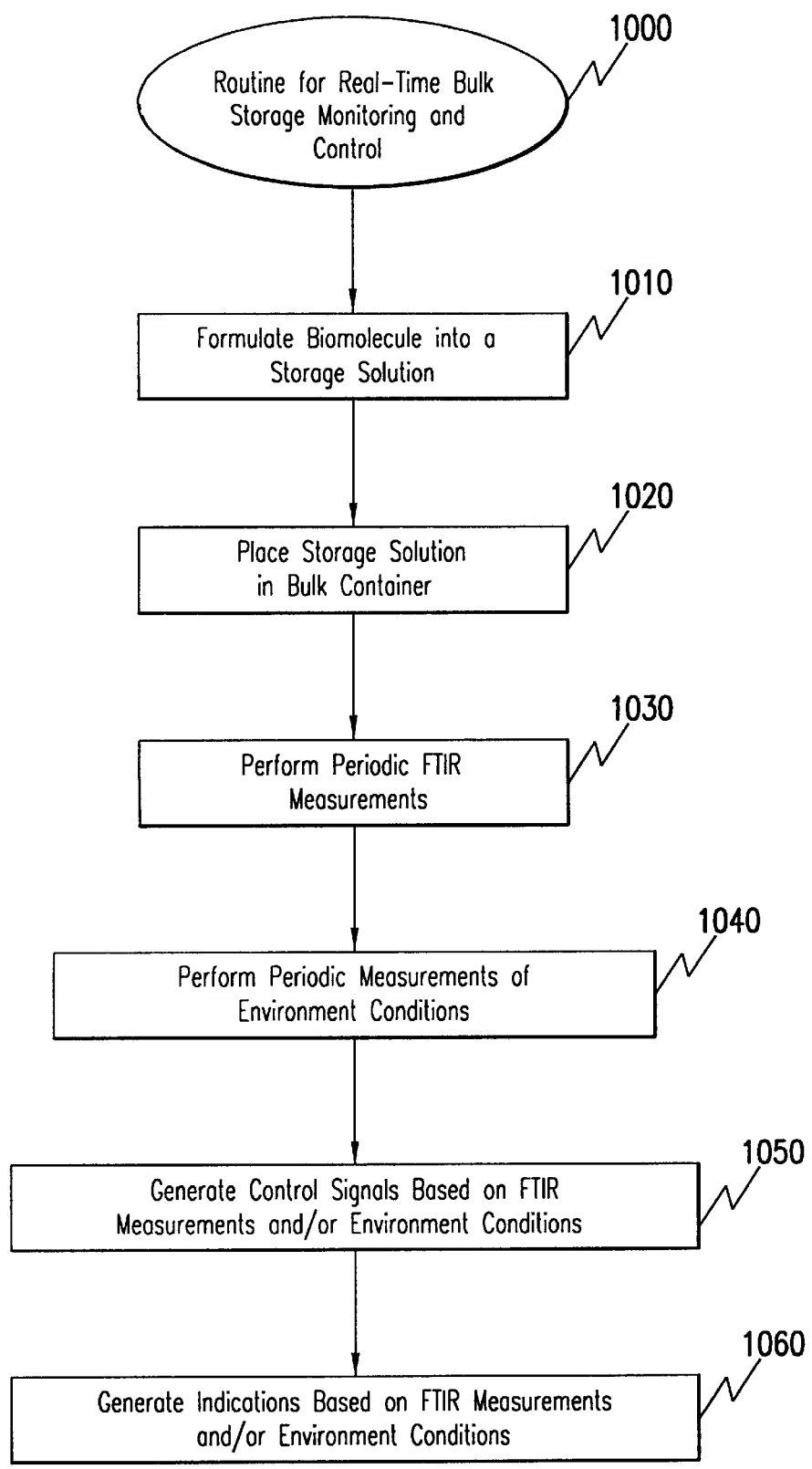
FIG. 10 is a flowchart of a routine for real-time bulk FTIR monitoring and control according to the present invention.

As introduced above, one embodiment of the present invention provides for real time, in situ IR monitoring of a biomolecule stored in bulk. Feedback controls are further provided to maintain optimal conditions for storage of the biomolecule. The structure and operation of this embodiment is further described with reference to example implementations shown in FIGS. 9 and 10. FIG. 9 is a diagram of a real-time bulk storage monitoring system 900 that includes FTIR monitoring and control. Real-time bulk storage monitoring system 900 includes a variety of probes and detection systems 200, 902, 910, 920, 930, 940 and 950 coupled to liquid bulk storage container 905. The FTIR probe 902 and system 200 and each of detectors 910–950 are connected to control mechanisms (e.g., temperature controller, gas feeds which are not shown) to maintain an ideal environment for storage of the pharmacologically active biomolecule. These connections are preferably made through a CPU or other processing means that can generate an appropriate control signal as described above, and as would be apparent to a person skilled in the art given this description. FIG. 10 is a flowchart of a routine 1000 for real-time bulk FTIR monitoring and control according to the present invention (steps 1010–1060). In the interest of brevity, each of the components of FIG. 9 is described with reference to steps 1010–1060 in routine 1000.

First, a biomolecule is formulated into a storage solution (step 1010). For example, formulation can include resuspending the biomolecule in a final solution containing physiologically acceptable excipients and carriers and/or lyophilizing the biomolecule formulation, and aseptically processing the formulation. A biomolecule with lability, such as Radio-Mabs, can be processed for bulk storage as well. Next, in step 1020, the biomolecule formulation is stored in bulk in container 905, awaiting finish and fill processes.

Periodic FTIR measurements are then made (step 1030). In one example shown in FIG. 9, bulk storage container 905 is fitted with a diamond IR probe 902, capable of measurements in the range of wave numbers from 300 to 5000 ($cm^{-1}$), and connected to an infrared spectrophotometer 200 as described above with respect to FIGS. 2 and 3. For example, FTIR system 200 can be a ReactIR™ 1000 system. Alternatively, a lyophilized bulk storage container is equipped with a germanium crystal internal reflection element connected to an infrared spectrophotometer, for example, a Bio-Rad FTS-7 system, equipped with a Hg/Cd/Te detector capable of measurements in the range of wave numbers from 300 to 5000 $cm^{-1}$. IR measurements of lyophilized samples is disclosed, for example, in Remmele et al., *Pharm. Res.* 14:1548–1555 (1997), which is incorporated by reference.

Container 905 is maintained in a controlled environment, usually at a temperature between about 0 and 5° C. for bulk storage in solution, and at a temperature between about −70 and 25° C., for lyophilized bulk storage, at a specific humidity and atmosphere. The biomolecule formulation is stored in contact with the FTIR probe 902. Since FTIR provides real time differentiation between active and inactive species of a biomolecule, the present invention will detect, in real time, any degradation of the formulation during storage, providing a continuous data stream of the specific activity of the bulk formulation. Such degradation might include, but is not limited to, the physical/chemical integrity or the preferred conformational arrangement of a biomolecule in the formulation. In so doing, the present invention allows precise definition of the pharmacological index of activity when it is sent for fill and finish. Thus, the present invention reduces or eliminates the need for overage in the finished product, allows for precise determination of activity, even when a product has a vary narrow pharmacological index. As used herein, the "pharmacological index" of a biomolecule formulation is the range acceptable pharmacological conditions where the biomolecule formulation retains sufficient bioactivity in the in vivo host.

In additional embodiments, a bulk storage container is monitored, in addition, for bioproduct degradation by temperature decay, UV light exposure and oxidation. Periodic measurements of environment conditions are performed (step 1040) measurements can include any one or combination of: measuring particle size with a particle size detector 910, measuring UV radiation with UV detector 920, measuring pH and/or conductivity with pH/conductivity detector(s) 930, measuring oxygen with oxygen detector 940, and measuring temperature with temperature sensor 950. Each of these variables has its own kinetics. In one embodiment, bulk storage container 905 is filled under anitrogen blanket in a headspace to prevent oxidation upon storage. In addition, bulk storage container 905 is fitted with oxygen sensor 940 to would allow measurement, over time of the amount of oxygen, versus nitrogen, present in the headspace of the container 905. In another embodiment, bulk storage container 905 is further fitted with UV detector 920. In additional embodiments, probes 930 are attached to measure, e.g., the pH, oxidation/reduction, and/or conductivity changes in the storage container 905.

Another aspect of maintaining ideal bulk storage is the degree to which the barrier provided by the storage container 905 actually is a true barrier. Usually, bulk storage containers comprise a plastic, e.g., polypropylene, or glass container, with a plastic or silicone seal. However, it is never possible to fully eliminate interaction with the environment. For example, interactions with the environment may cause some slow inorganic reactions. For example, $CO_2$ stripped off of carbonate may become part of another molecule, e.g., ammonium magnesium carbonate, which falls out of solution. In certain embodiments of the present invention, bulk storage containers are monitored for such precipitates, for example, by use of visible light particle size detector(s) 910. Such particle size detector(s) 910 can detect transmitted, reflected, and/or scattered light in the storage solution.

In step 1050, control signals are then generated based on FTIR measurements made in step 1030. For example, as mentioned above, since FTIR provides real time differentiation between active and inactive species of a biomolecule, any degradation of the formulation during storage is readily detected. Based on a stability curve and the real-time monitoring of FTIR spectra of an active biomolecule, a control signal can be generated to increase or lower temperature. A control signal can also be generated to increase or decrease a gas feed for nitrogen. In this way the rate of degradation can be slowed. The timing of degradation is also monitored precisely. In so doing, the present invention allows precise definition of the pharmacological index of activity when it is sent for fill and finish. Thus, the present invention reduces or eliminates the need for overage in the finished product, allows for precise determination of activity, even when a product has a vary narrow pharmacological index.

In step 1050, control signals can also be based on other environment conditions measured in step 1040. For example, based on a stability curve and the real-time measurements of environment conditions (e.g., particle size, pH/conductivity, UV, oxygen, and temeprature), one or more control signals can be generated to increase or lower temperature, and to increase or decrease a gas feed for nitrogen. In this way the rate of degradation can be slowed as immediate feedback controls to the environment of the bulk storage are provided to maintain an optimal environment.

In step 1060, indication signals can also be generated based on FTIR measurements made in step 1030 and/or other environment conditions measured in step 1040. For example, based on a stability curve and the real-time measurements of environment conditions (e.g., particle size, pH/conductivity, UV, oxygen, and temeprature), one or more indication signals can be generated to generate an alarm (visual, audible and/or tactile), or to display to data representing the FTIR spectra measured or the actual environment conditions measured. In this way, a user is provided with real-time indications of bulk storage conditions, including a real-time indication of the presence of an active biomolecule concentration in the storage solution in container 905.

B. Automated Accelerated Storage Studies Based on FTIR Monitoring

Currently available stability studies involve putting samples in a number of chambers, holding the chambers at various elevated temperatures for various periods of time, and generating a table of data to determine the stability contour based on the arrenious equation. The presently available studies all are extremely expensive and time-consuming.

In contrast, in another embodiment of the present invention, real-time IR monitoring and control of bulk storage of formulations can be applied in automated, accelerated stability studies. In-line, in situ FTIR monitoring is used to rapidly determine and bracket the stability range for a pharmacologically active biomolecule in its final formulation, or in proposed formulations.

Figure 11A:
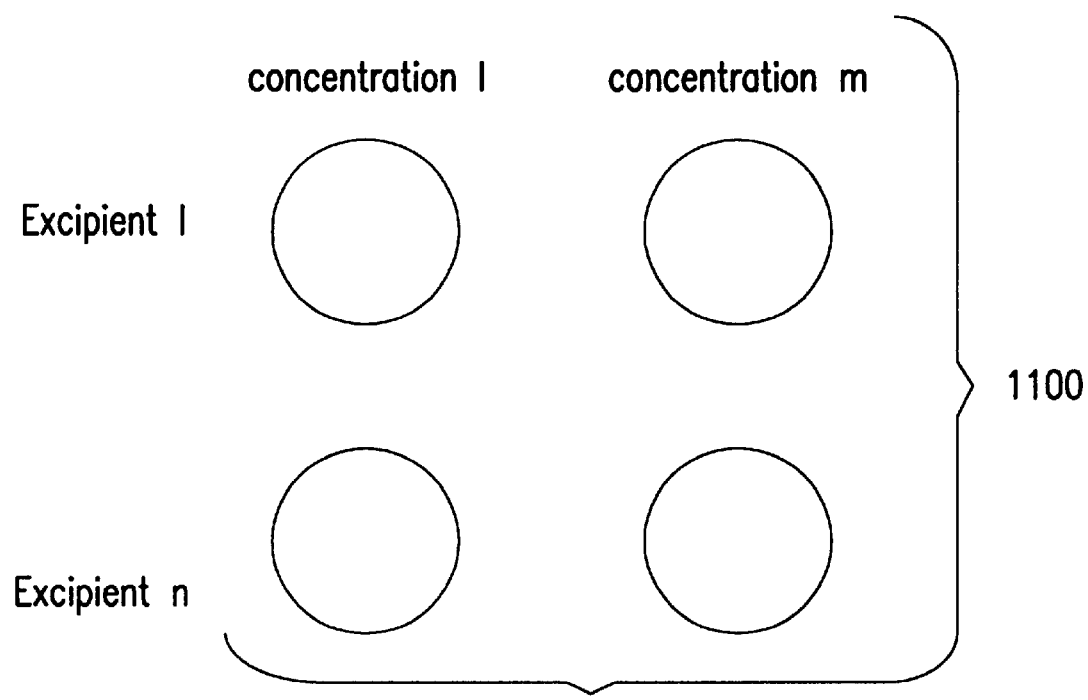
FIGS. 11A and 11B are diagrams of a system for automated accelerated storage studies including FTIR monitoring and control according to another embodiment of the present invention.
Figure 11B:
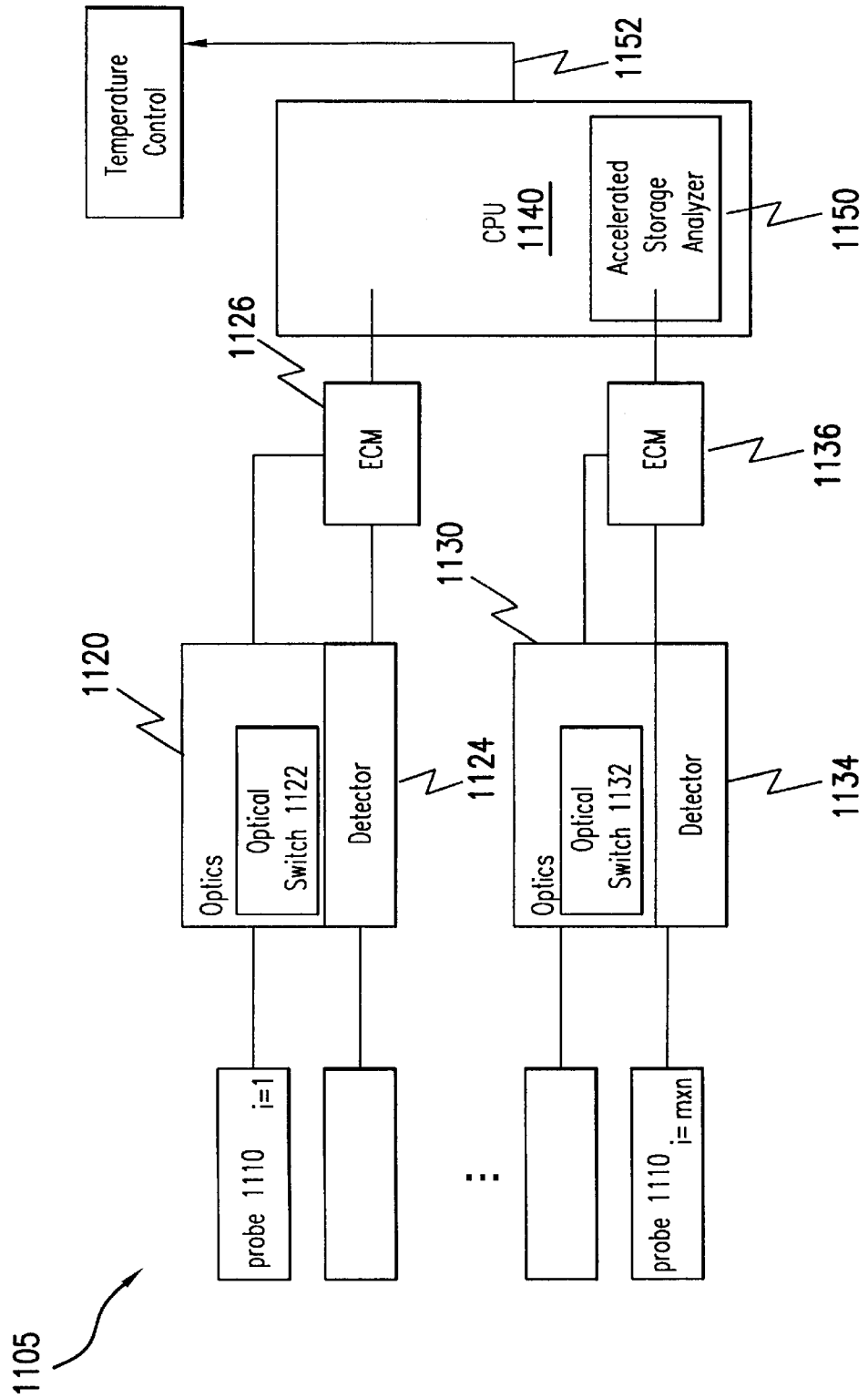
Figure 12:
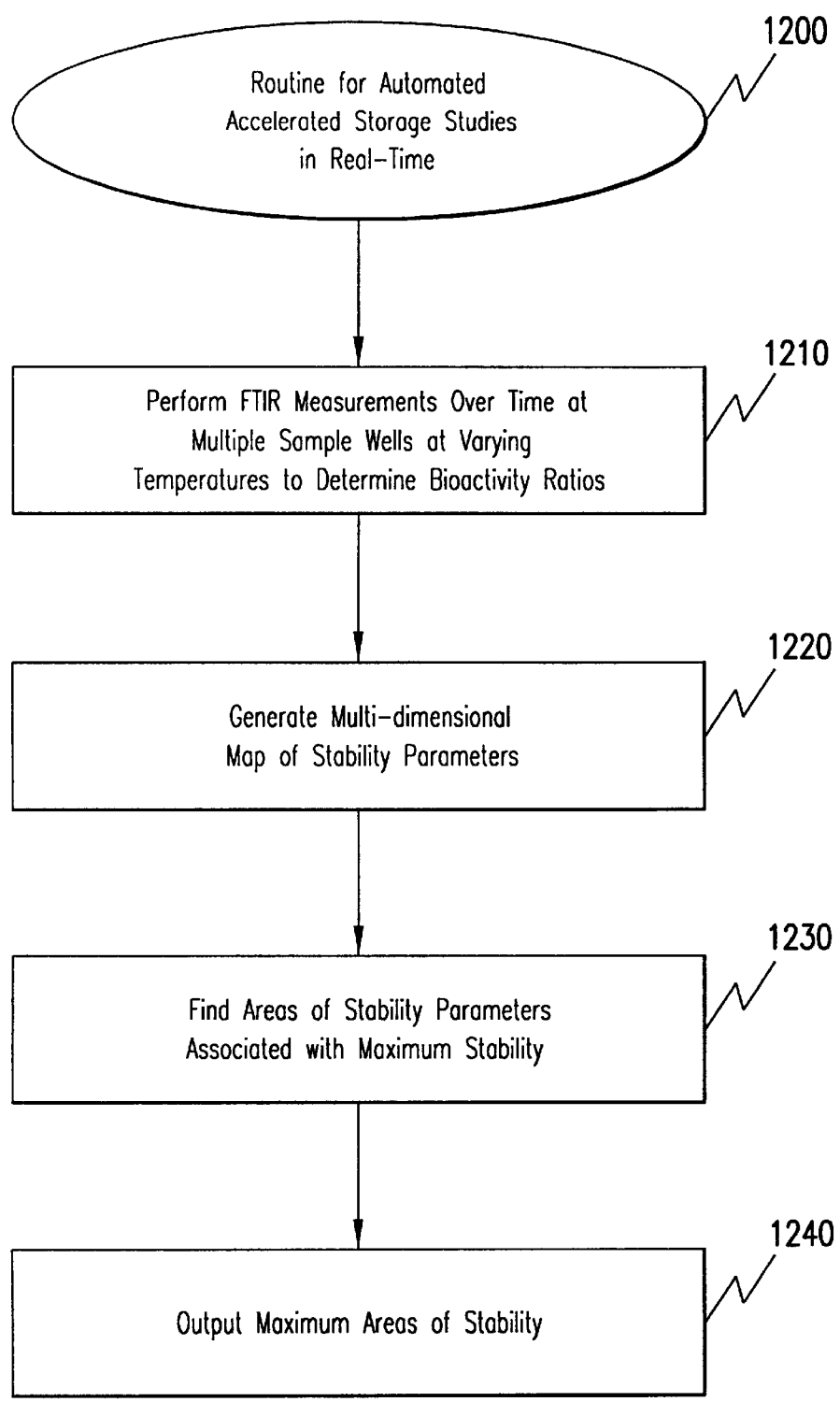
FIG. 12 is a flowchart of a routine for automated accelerated storage studies including FTIR monitoring and control according to the present invention.

The structure and operation of this embodiment is described with respect to example implementations shown in FIGS. 11A, 11B, and FIG. 12. In particular, FIGS. 11A and 11B are diagrams of a system for automated accelerated storage studies including FTIR monitoring and control according to another embodiment of the present invention. FIG. 12 is a flowchart of a routine for automated accelerated storage studies including FTIR monitoring and control according to the present invention.

As shown in FIG. 11A, samples of a bulk formulation of a biomolecule are kept in an array of wells (also called chambers or containers) for varying times and at varying temperatures, oxygen levels, nitrogen levels, UV/visible light levels, and (for lyophilized samples) humidity levels. Preferably, the array of wells are kept under more extreme conditions than normal to accelerate the aging process of the formulation. Each well is monitored by FTIR, in real time, for the proportion of active and inactive forms of the biomolecule. The curve generated from this data allows the skilled artisan to predict the rest of the curve, i.e., the long term stability of the formulation. In one example, each well in the array has a unique excipient and concentration. For example, the array of wells 1100 consists of n sets of wells corresponding to n different excipients. Each set of wells at a particular excipient consists of m wells corresponding to m different concentrations. In one preferred embodiment, an array of 96 wells is used.

In one example, for monitoring, e.g., temperature, each set of wells is individually temperature controlled, and each is equipped with an FTIR monitor with a sensor. Thus, a matrix of concentrations and solutions can be measured in a single block. By varying the temperatures in that block, and by using a miniaturized format, a stability study, which normally might take years to complete, could be completed in a day.

FIG. 11B shows an example FTIR system 1105 that can be used to monitor in real-time the array of wells 1100. FTIR system 1105 includes an array of probes 1110, where i=1 to m×n. Depending upon the number of wells and other mechanical or size limitations, each probe tip (also called a sensor) is an attenuated total reflection (ATR) element. This ATR element can be a diamond, silicon, or cubic zirconia wafer or prism, or a fiber optic tip. In one example, each probe 1110$i$ is a sensor 210 and can be part of an associated FTIR system 200 as described above.

In the example of FIG. 11B, to save space and reduce cost, a pair of probes 1110$i$ share a common optics module 1120, optical switch 1122, and electronics control module ECM 1126. The optical switch 1122, under the control of CPU 1140, switches to provide signals representative of FTIR spectra from either of the pair of sensors 1110$i$ to detector 1124. Likewise, another pair of probes 1110$i_{m \times n}$ share a common optics module 1130, optical switch 1132, and electronics control module ECM 1136. In the example of FIG. 11B, a 2:1 ratio of probes 1110$i$ to detectors is used; however, greater ratios can be used.

Each of the electronics controls module 1126, 1136 and detectors 1124, 1134 are coupled to one or more CPUs 1140. CPU(s) 1140 essentially perform all of the processing related to FTIR measurement as described above in general, and in particular, as described with respect to CPU 250. CPU(s) 1140 further includes an accelerated studies analyzer 1150. Accelerated studies analyzer 1150 can be software, firmware, and/or hardware for carrying out routine 1200 for automated accelerated storage studies in real-time. The operation of the array of wells 1100 and FTIR-based accelerated studies system 1105 is described further with reference to routine 1200 shown in FIG. 12.

Routine 1200 provides the ability to do automated, accelerated stability studies in real time (steps 1210–1240). In step 1210, FTIR measurements are performed in each well of the array of wells 1100. These FTIR measurements arr performed at varying temperatures to determine bioactivity ratios. In one preferred example, the temperature in the wells 1100 is varied over time, but at a much accelerated rate. Background scans are taken on the material, and the FTIR output is adjusted to measure the biomolecule in the environment of the various excipients, i.e., the stability of the formulation. Once the background is determined, the temperature is varied, and allowed to progress over time to get a "decay curve." The instantaneous slope at any particular temperature for the decay curve is then determined.

From this data, a multi-dimensional map of stability parameters (temperature, time, bioactivity) is generated (step 1220). The data is graphed in three dimensions: z=bioactivity ratio, i.e., the ratio of the pharmacologically active biomolecule vs. the inactive forms as measured by FTIR, x=temperature, and y=time. A pattern analysis is then used to find areas (points or ranges) of stability parameters associated with maximum stability (step 1230). Stability of the biomolecule is determined based on heuristic analysis or contour mapping, such as, contour mapping of an Arrenious equation. The contour map is analyzed to find wells or valleys of higher stability.

In additional embodiments, further parameters can be monitored in addition to temperature and time, for example, the stability of the biomolecule can be measured as a function of different levels and kinds of excipients. Using this approach, multiple contour maps can be analyzed to find out which combinations give you the best stability.

Finally, the areas (points or ranges) of stability parameters found in step 1230 are then output (step 1240). Such output can be provided in the form of a display, print out, or other indication, and can be stored in electronic form for further use by an operator or user.

This approach of routine 1200 allows stability studies to be accomplished in a much shorter time period and at a far less cost than was previously possible. In particular, doing FTIR monitoring in a multiplex array format, the skilled artisan could be measuring anywhere from two up to one thousand or more variables at one time.

VII. Example Computer System

Figure 8:
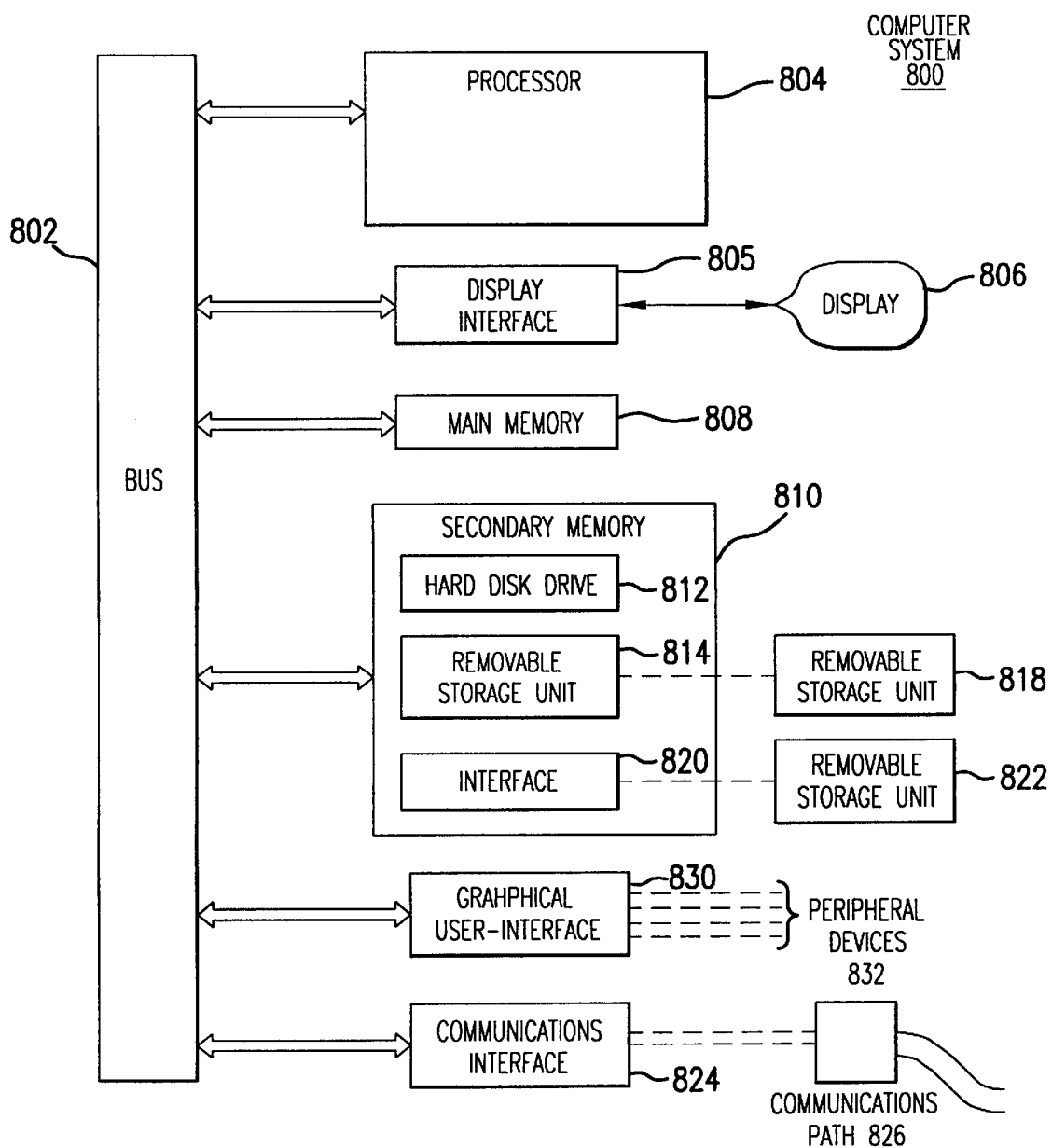
FIG. 8 is a diagram of a computer system according to an embodiment of the present invention.

As described above, CPUs 250, 1140 can be any type of computer including but not limited to a personal computer, desktop computer, laptop computer, workstation, mid-range or high-range computer. An example of such a computer system that can be used in the present invention is shown in FIG. 8. Computer system 800 represents any single or multi-processor computer. Single-threaded and multi-threaded computers can be used. Unified or distributed memory systems can be used.

Computer system 800 includes one or more processors, such as processor 804. One or more processors 804 can execute software implementing routine 100 as described in FIG. 1 above. Each processor 804 is connected to a communication infrastructure 802 (e.g., a communications bus, cross-bar, or network). Various software embodiments are described in terms of this exemplary computer system. After reading this description, it will become apparent to a person skilled in the relevant art how to implement the invention using other computer systems and/or computer architectures.

Computer system 800 also includes a main memory 808, preferably random access memory (RAM), and can also include a secondary memory 810. The secondary memory 810 can include, for example, a hard disk drive 812 and/or a removable storage drive 814, representing a floppy disk drive, a magnetic tape drive, an optical disk drive, etc. The removable storage drive 814 reads from and/or writes to a removable storage unit 818 in a well known manner. Removable storage unit 818 represents a floppy disk, magnetic tape, optical disk, etc., which is read by and written to by removable storage drive 814. As will be appreciated, the removable storage unit 818 includes a computer usable storage medium having stored therein computer software and/or data.

In alternative embodiments, secondary memory 810 may include other similar means for allowing computer programs or other instructions to be loaded into computer system 800. Such means can include, for example, a removable storage unit 822 and an interface 820. Examples can include a program cartridge and cartridge interface (such as that found in video game devices), a removable memory chip (such as an EPROM, or PROM) and associated socket, and other removable storage units 822 and interfaces 820 which allow software and data to be transferred from the removable storage unit 822 to computer system 800.

Computer system 800 can also include a communications interface 824. Communications interface 824 allows software and data to be transferred between computer system 800 and external devices via communications path 826. Examples of communications interface 824 can include a modem, a network interface (such as Ethernet card), a communications port, etc. Software and data transferred via communications interface 824 are in the form of signals which can be electronic, electromagnetic, optical or other signals capable of being received by communications interface 824, via communications path 826. Note that communications interface 824 provides a means by which computer system 800 can interface to a network such as the Internet.

The present invention can be implemented using software running (that is, executing) in an environment similar to that described above with respect to FIG. 8. In this document, the term "computer program product" is used to generally refer to removable storage unit 818, a hard disk installed in hard disk drive 812, or a carrier wave or other signal carrying software over a communication path 826 (wireless link or cable) to communication interface 824. A computer useable medium can include magnetic media, optical media, or other recordable media, or media that transmits a carrier wave. These computer program products are means for providing software to computer system 800.

Computer programs (also called computer control logic) are stored in main memory 808 and/or secondary memory 810. Computer programs can also be received via communications interface 824. Such computer programs, when executed, enable the computer system 800 to perform the features of the present invention as discussed herein. In particular, the computer programs, when executed, enable the processor 804 to perform the features of the present invention. Accordingly, such computer programs represent controllers of the computer system 800.

In an embodiment where the invention is implemented using software, the software may be stored in a computer program product and loaded into computer system 800 using removable storage drive 814, hard drive 812, or communications interface 824. Alternatively, the computer program product may be downloaded to computer system 800 over communications path 826. The control logic (software), when executed by the one or more processors 804, causes the processor(s) 804 to perform the functions of the invention as described herein.

In another embodiment, the invention is implemented primarily in firmware and/or hardware using, for example, hardware components such as application specific integrated circuits (ASICs). Implementation of a hardware state machine so as to perform the functions described herein will be apparent to persons skilled in the relevant art(s).

VIII. EXAMPLES

Having generally described the invention, the same will be more readily understood by reference to the following example, which is provided by way of illustration and is not intended to be limiting. Other recovery and purification methods to which IR spectroscopic monitoring and control may be applied will be readily apparent to one skilled in the art.

Example 1

Biomanufacturing Process for Human Interleukin-10 Produced in *Escierichia coli* Using FTIR Monitoring and Control Biomanufacturing of an example biomolecule, human interleukin-10 (hIL-10), using FTIR monitoring and control is carried out by the following improved method, based on a method described in U.S. Pat. No. 5,710,251, which is incorporated herein by reference. FTIR monitoring is carried out using IR radiation in a range of 10–14,000 wavenumber ($cm^{-1}$), and preferably, 400–4,000 wavenumber ($cm^{-1}$). Near-IR and Far-IR radiation can be used.

A. Fermentation

*Escherichia coli* (*E. coli*) transformed with an expression plasmid containing a gene encoding and expressing recombinant human Interleukin-10 (IL-10), for example, rhuIL-10, is available from the American Type Culture Collection, for example, as Accession Number 68191. This plasmid, upon temperature induction, expresses recombinant human IL-10 intracellularly as insoluble inclusion bodies.

A 1.5 ml frozen vial of rhuIL-10 is thawed at room temperature. Approximately 0.5 ml is transferred into a 2000 ml flask containing 500 ml of a culture medium comprising 30 g/L casamino acids, 20 g/L yeast extract, 5 g/L $KPO_4$, 20 g/L glycerol, 1 g/L $MgSO_4$ and 10 mg/L tetracycline, pH 7. The flask 5 is placed on a rotary shaker and shook at 300 RPM at 30° C. After 6.5–7 hrs a sample is removed from the flask for optical density determination, to ensure the attainment of log-phase growth. A 1000 liter fermentation reactor as depicted in FIG. 5 is prepared, containing 800 liters of culture medium comprising, for example, 30 g/l Casein Digest-HyCase P (Sheffield), 20 g/l Yeast Extract, 15 g/l Potassium Phosphate-Monobasic, 0.5 ml/l of a 30% suspension of SAG-471® (Union Carbide), 20 g/l Glucose, 1 g/l Magnesium Sulfate-7 $H_2O$, 10 mg/l tetracycline, and 2 ml/l Iron Citrate Stock Solution comprised of 2 ml/I sulfuric acid, 15 g/l Sodium Citrate, and 13.5 g/l Ferric Chloride Hexahydrate. The pH of the medium is adjusted to about 7 with a solution of 50% NaOH and a solution of 75% $H_3PO_4$. The fermentor is then inoculated with the contents of the 2000 ml flask. The temperature of the inoculated medium within the fermentor is maintained at 30° C.±0.5 ° C. for the first part of the fermentation reaction. During this part of the fermentation, homeostasis for log growth is maintained in the fermentation reactor by direct, real time, in situ FTIR monitoring of (a) glucose concentration, (b) organic volatile acid concentration, (c) ammonium ion concentration, (d) dissolved $O_2$ and $CO_2$ concentrations, and (e) inorganic metabolic ions (e.g., $PO_4^{2-}$, $SO_4$), with feedback control provided for the rates of (1) glucose feed, (2) agitation, and (3) $O_2$ and air feeds, in particular to maintain the dissolved oxygen concentration in the fermentor at a level greater than 40% of saturation. When optimal growth in the fermentation reaction is achieved, as measured by FTIR in conjunction with the attached OD probe 580, the culture is automatically induced by a feedback control adjustment, raising the temperature of the fermentation reactor to 38° C.±0.5° C. The fermentation reaction is maintained at this temperature for an additional for 14 hours to allow for the recombinant protein expression.

The fermentation reactor is harvested by centrifugation using, for example, a contained CSA-16 continuously desludging centrifuge at a feed flowrate of approximately 5–10 liters per minute (1 pm). About 40 kg of cell paste is recovered in the centrifugation step.

B. Recovery

The recovery stage is carried out essentially as depicted in FIG. 6, but FTIR monitoring and control is provided only at the refolding step. References to the recovery steps of FIG. 6 are provided.

Cell breakage 620. The cell paste recovered in the centrifugation step is homogenized using, for example, a Gaulin M12 homogenizer at an operating pressure of 7000–8000 psi for the equivalent of 6 passes. Homogenization is continued until greater than about 95% cell breakage is observed in a sample of the homogenate withdrawn and examined under a phase contrast microscope.

Extraction 640. The homogenized cells are extracted with an equal volume of a buffer comprising 6.05 g/l Tris-HCl, 1.90 g/l disodium EDTA dihydrate, 58.4 g/l NaCl USP, and 382 g/l Guanidine HCl. The resuspension is held for 30 min. at 10 to 15° C. under slow agitation. The inactivated resuspension is then centrifuged in, for example, a Sharples AS26SP centrifuge at a flowrate of 500 ml per minute and a centrifuge speed of 17000 rpm. A pellet containing inclusion bodies is recovered in this step and is frozen at −10° C.

Denaturation 660. The inclusion body pellet is thawed slowly for three days at 2 to 10° C. in a cold room. The pellet is broken up and added to 20 liters of a buffer comprised of 50 mM Tris-HCl, 7M guanidine HCl, and 4 mM dithiothreitol (DTT), pH 8.5. The inclusion body pellet is vigorously agitated with a polytron homogenizer to form a fine suspension. This suspension is then allowed to solubilize by slow agitation for approximately 3 hours at 2 to 10° C.

Refolding 680. The protein solution is then diluted approximately twenty five fold into a refolding buffer comprising, for example, 50 mM Tris-HCl, 0.12M Guanidine HCl, and 0.05 mM Glutathione (reduced), pH 8.5. The diluted solution is immediately clarified by filtration, and introduced into a closed tank fitted with a recirculating flow cell which comprises an FTIR detector. The tank further comprises a gas feed which provides controlled introduction of $O_2$, nitrogen, or a mixture thereof. An oxidized glutathione solution is then added to a 0.45 mM final concentration. FTIR measurements are taken at intervals ranging from every second to every hour, preferably at intervals ranging from every 10 seconds to every 10 minutes, and even more preferably at intervals ranging from every 20 seconds to every 5 minutes. At each measurement, the FTIR spectra of hIL-10 in the refolding solution is monitored and compared to a reference spectra of pharmacologically active hIL-10, using the algorithm depicted in FIG. 3. In order to optimize refolding, the oxidation reaction is controlled, in real time, by the input of an air/oxygen mixture. When the the refolding step has reached a preset or optimal amount of the pharmacologically active form, the refolding mixture is automatically shunted to the next step in the process.

Concentration/Diafiltration 690. At the end of the refolding step, the solution is clarified by filtration through an in-line 0.45 μm filter. The solution containing the refolded IL-10 is concentrated approximately 10 fold using, for example, a Millipore PELLICON® ultrafilter with 10,000 nominal molecular weight PLGC membranes. The concentrate is then diafiltered in a buffer comprising 20 mM Tris-HCl and 20 mM NaCl at pH 8.5.

C. Purification

Each chromatographic separation step depicted below is carried out in a system similar to that depicted in FIG. 7. Reference to the elements in FIG. 7 are provided.

Cation Exchange Chromatography. The concentrated solution containing refolded hIL-10 is adjusted to 20 mM BIS-Tris, pH 6.5 by addition of 1M BIS-Tris and 4N HCl. The solution is then clarified by in-line filtration, and is run through a flow cell 745 comprising an FTIR monitor. The solution is monitored for the optimal proportion of the pharmacologically active form if hIL-10, using the algorithm depicted in FIG. 3. If the protein solution contains an excess proportion of hIL-10 having an FTIR spectra indicative of an inactive form of the biomolecule, the solution is shunted back for additional refolding, or, in some situations, discarded. If the optimal form is detected by FTIR, the clarified feed solution is then applied, for example, to a 12 liter (e.g., 12 cm×36 cm diameter) S-SEPHAROSE® Fast Flow sulfonate column 710 (Pharmacia, Piscataway, N.J.) at a rate of 1 cm/min. The column is pre-equilibrated with ten bed volumes of a pH 6.5, 20 mM BIS-Tris, 0.065M NaCl buffer, pH 6.5. A flow cell comprising an FTIR monitor 745 is situated in line below column 710. The flow-through of the column is monitored for excess amounts of active hIL-10. If excess amounts are detected in the flow-through (e.g., if concentration of hIL-10 present in flow-through is above acceptance criteria), it is shunted through the column one or more additional times to allow for complete binding of the active hIL-10 to the column. When the active hIL-10 is optimally bound to the column, and the column washed with equilibration buffer, elution is performed with a 20 column volume gradient in the range of 0.065–0.4M NaCl, 20 mM BIS-Tris, pH 6.5 buffer at a rate of 0.5 cm/min. The elution gradient is run through the in-line FTIR monitor. Resolution of the elution is adjusted by feedback control to the gradient mixer 725, adjusting the curve of the gradient, and pump speed 730, adjusting the flow speed through the column. Fractions containing active hIL-10 in acceptable proportion with impurities are detected and collected by diverting those fractions to a pool for further processing.

Anion Exchange Chromatography. The pooled fractions from the cation exchange chromatography process containing hIL-10 are concentrated by ultrafiltration as described in the recovery step, supra. The concentrate is then diafiltered using 10 mM Tris-HCl, pH 8.7. The concentration is then run through a flow cell 745 comprising an FTIR monitor. The solution is monitored for the optimal proportion of the pharmacologically active form if hIL-10, using the algorithm depicted in FIG. 3. If the protein solution contains an excess proportion of hIL-10 having an FTIR spectra indicative of an inactive form of the biomolecule, the solution is shunted back for reprocessing, or, in some situations, discarded. The solution is then applied to a 6 liter (e.g., an 18 cm×23.5 cm) quaternary ammonium column Q-SEPHAROSE® Fast Flow (Pharmacia) at a flow rate of 0.5 cm/min, pre-equilibrated with 10 mM TRIS, 8 mM NaCl, pH 8.7 buffer. The column flow-through is monitored by FTIR as described above. The pharmacologically active form of hIL-10 has a differential attraction to the resin versus inactive forms, and is separated by elution with 10 mM TRIS, 8 mM NaCl, pH 8.7 buffer. Elution of pharmacologically active vs. inactive forms of hIL-10 is monitored by FTIR, with feedback control provided to adjust the elution buffer composition to finely resolve separation of active and inactive forms of hIL-10. Fractions containing the pharmacologically active form of hIL-10 in acceptable proportion with impurities, as detected by FTIR, are pooled for further purification.

Hydroxyapatite Chromatography. The pool containing pharmacologically active hIL-10, as obtained from the anion exchange chromatography step, is monitored for the optimal proportion of the pharmacologically active form if hIL-10, using the algorithm depicted in FIG. 3. If the protein solution contains an excess proportion of hIL-10 having an FTIR spectra indicative of an inactive form of the biomolecule, the solution is shunted back for reprocessing, or, in some situations, discarded. The solution is then applied to a 4 liter (e.g., a 26 cm×14 cm diameter) hydroxyapatite column, for example, a Biorad MACRO-PREP column, pre-equilibrated with 20 mM Tris, 20 mM NaCl, pH 7.4 buffer. The flow-through is monitored by FTIR for non-binding of hIL-10 to the column, as described for the anion exchange chromatography step, supra. A column wash is performed by decreasing the amount of 20 mM Tris buffer from 100% to 95% and increasing the level of pH 7.4, 0.15M sodium phosphate buffer 0% to 5% for approximately 4 column volumes. The flow through from this step is monitored by FTIR, similarly to the description under the anion exchange step, supra. The elution is performed by increasing the percent of phosphate buffer gradient from 5% to 100% elution of pharmacologically active vs. inactive forms of hIL-10 is monitored by FTIR, with feedback control provided to adjust the elution buffer composition and gradient curve to finely resolve separation of active and inactive forms of hIL-10. Fractions containing the pharmacologically active form of hIL-10, as detected by FTIR, are pooled for further purification.

Gel Filtration Chromatography. The pool from the hydroxyapatite chromatography step containing pharmacologically active hIL-10, is concentrated by ultrafiltration as described, supra. The concentrate is then monitored for the optimal proportion of the pharmacologically active form if hIL-10, using the algorithm depicted in FIG. 3. If the protein solution contains an excess proportion of hIL-10 having an FTIR spectra indicative of an inactive form of the biomolecule, the solution is shunted back for reprocessing, or, in some situations, discarded. The solution is then applied to a gel filtration column, for example, a SEPHACRYL® S-200 HR column, pre-equilibrated with 10 mM Tris buffer, pH 7.4. The column is eluted with a pH 7.4, 10 mM TRIS buffer. Elution of pharmacologically active vs. inactive forms of hIL-10 is monitored by FTIR, with feedback control provided to adjust the elution speed at pump 730 to finely resolve separation of active and inactive forms of hIL-10. Fractions containing the pharmacologically active form of hIL-10, as detected by FTIR, are pooled, and filtered through an in-line 0.2 μm filter. The filtrate, after a final FTIR measurement, is stored at about 0 to 4° C.

D. Bulk Storage

The purified hIL-10 solution is kept in a container, equipped with an FTIR probe, in a controlled environment, at a temperature between about 0 and 5° C., at a specific humidity and atmosphere. FTIR is used to provide real time monitoring of the proportion of pharmacologically active hIL-10 being stored. FTIR detects, in real time, degradation of the formulation during storage, and provides a continuous data stream of the specific activity of stored formulation. When it is time to send the formulation for fill and finish, the data provided by FTIR allows and exact determination of the specific activity of the solution. Additionally, FTIR monitoring during bulk storage feedback controls to the environment of the bulk storage, in particular the storage temperature, to maintain an optimal environment for the pharmacologically active molecule.

IX. Conclusion

While specific embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for controlling a biomanufacturing process for a biomolecule, comprising the steps of:
    detecting an infra-red spectra in situ and in real-time of said biomolecule during at least a bulk formulation and storage stage of said biomanufacturing process, wherein said infra-red spectra characterizes a fingerprint of said biomolecule; and
    generating at least one control signal in response to the detected infra-red spectra, wherein said at least one control signal enables a control step in said biomanufacturing process.

2. The method of claim 1, wherein said biomanufacturing process comprises:
    a recovery stage;
    a purification stage; and
    a bulk formulation and storage stage; and wherein said generating step and said detecting step are each performed during the recovery stage, the purification stage, and the bulk formulation and storage stage; whereby a desired quality control is maintained during the biomanufacturing process.

3. A method for controlling a biomanufacturing process for a secreted protein, comprising the steps of:
    detecting an infra-red spectra in situ and in real-time of a secreted protein during at least one stage of said biomanufacturing process, wherein said infra-red spectra characterizes a fingerprint of said secreted protein; and
    generating at least one control signal in response to the detected infra-red spectra, wherein said at least one control signal enables a control step in said biomanufacturing process.

4. The method of claim 3, wherein said fingerprint of said secreted protein is characteristic of a secondary structure of said secreted protein.

5. The method of claim 4, and further comprising performing the control step in response to said at least one control signal, wherein said control step maintains or restores a desired secondary structure of said secreted protein.

6. The method of claim 5, wherein said desired secondary structure is an active form of said secreted protein.

7. The method of claim 3, further comprising a bioproduction stage.

8. The method of claim 7, wherein said bioproduction stage comprises a process selected from the group consisting of: fermentation, cell culture, semisynthetic bioprocessing, extractive processes, catabolic processes, and production of therapeutic viruses.

9. The method of claim 8, wherein said bioproduction stage comprises a fermentation reaction, and further comprising the step of:
    detecting an infra-red spectra of said fermentation in situ and in real-time; and
    generating at least one control signal in response to said infra-red spectra of said fermentation, whereby homeostasis of said fermentation reaction can be maintained.

10. The method of claim 9, further comprising performing an adjustment of the conditions of said fermentation reaction in response to the at least one control signal generated in response to said infra-red spectra of said fermentation, said adjustment being selected from the group consisting of: a glucose feed adjustment, a gas feed adjustment, a salts and vitamin feed adjustment, an ammonium hydroxide adjustment, a temperature adjustment, and an agitation speed adjustment.

11. The method of claim 3, further comprising a recovery stage.

12. The method of claim 11, wherein said recovery stage comprises at least one recovery step.

13. The method of claim 12, wherein said recovery step is selected from the group consisting of: cell breakage, extraction, denaturation, refolding, oxidation, diafiltration, lyophilization, and concentration.

14. The method of claim 12, wherein said recovery stage comprises a refolding reaction.

15. The method of claim 14, further comprising performing a recovery control step in said refolding reaction in response to the at least one control signal generated in said generating step.

16. The method of claim 15, wherein said recovery control step comprises regulating the rate of oxidation in said refolding reaction.

17. The method of claim 16, wherein said recovery control step regulates a gas feed to said refolding reaction.

18. The method of claim 3, further comprising a purification stage.

19. The method of claim 18, wherein said purification stage comprises at least one purification step.

20. The method of claim 19, wherein said purification step comprises a process selected from the group consisting of: precipitation, continuous sucrose gradient centrifugation, filtration, electrophoresis, and chromatographic separation.

21. The method of claim 20, wherein said chromatographic separation process comprises a step selected from the group consisting of: anion exchange chromatography, cation exchange chromatography, gel filtration chromatography, hydrophobic interaction chromatography, chromatofocusing, hydroxylapatite chromatography, and affinity chromatography.

22. The method of claim 21, comprising the steps of:
    detecting an infra-red spectra of the flow-through from said chromatography step in situ and in real-time; and generating at least one control signal in response to said infra-red spectra of the flow-though, wherein said at least one control signal enables at least one flow-through control step in said chromatography step.

23. The method of claim 22, wherein said at least one flow-through control step comprises controlling a shunt to allow repetition of said chromatography step.

24. The method of claim 21, comprising the steps of:
detecting an infra-red spectra of the eluate from said chromatography step in situ and in real time; and
generating at least one control signal in response to said infra-red spectra of the eluate, wherein said at least one control signal enables at least one elution control step in said chromatography step.

25. The method of claim 24, wherein said at least one elution control step comprises performing an adjustment to said chromatography step selected from the group consisting of adjustment of the elution gradient curve, adjustment of the temperature, and adjustment of the flow rate.

26. The method of claim 3, further comprising a bulk formulation and storage stage.

27. The method of claim 3, wherein said biomanufacturing process comprises:
a recovery stage;
a purification stage; and
a bulk formulation and storage stage; and wherein said generating step and said detecting step are each performed during the recovery stage, the purification stage, and the bulk formulation and storage stage; whereby a desired quality control is maintained during the biomanufacturing process.

* * * * *